United States Patent
Cohen et al.

(10) Patent No.: US 12,268,355 B2
(45) Date of Patent: Apr. 8, 2025

(54) DISCRIMINATION OF CALCULI AND TISSUES WITH MOLECULAR CHEMICAL IMAGING

(71) Applicant: CHEMIMAGE CORPORATION, Pittsburgh, PA (US)

(72) Inventors: Jeffrey Cohen, Pittsburgh, PA (US); Patrick Treado, Pittsburgh, PA (US); Shona Stewart, Pittsburgh, PA (US); Heather Gomer, Sewickley, PA (US); Arash Samiei, Pittsburgh, PA (US); Alyssa Zrimsek, Pittsburgh, PA (US); Jihang Wang, Sewickley, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 0 days.

(21) Appl. No.: 17/582,764

(22) Filed: Jan. 24, 2022

(65) Prior Publication Data
US 2022/0142457 A1     May 12, 2022

Related U.S. Application Data

(63) Continuation of application No. 16/544,499, filed on Aug. 19, 2019, now Pat. No. 11,229,400.

(60) Provisional application No. 62/719,462, filed on Aug. 17, 2018.

(51) Int. Cl.
| | |
|---|---|
| A61B 1/00 | (2006.01) |
| A61B 1/06 | (2006.01) |
| A61B 5/00 | (2006.01) |
| G01N 21/25 | (2006.01) |

(52) U.S. Cl.
CPC ...... *A61B 1/000094* (2022.02); *A61B 1/0638* (2013.01); *A61B 1/0646* (2013.01); *A61B 5/4887* (2013.01); *G01N 21/25* (2013.01)

(58) Field of Classification Search
None
See application file for complete search history.

(56) References Cited

U.S. PATENT DOCUMENTS

| | | | |
|---|---|---|---|
| 5,111,038 A | * | 5/1992 | Taylor .................. G01S 7/4802 356/73 |
| 8,098,373 B2 | | 1/2012 | Nelson et al. |
| 2003/0156788 A1 | | 8/2003 | Henning |
| 2005/0065440 A1 | * | 3/2005 | Levenson ............ G01N 21/255 356/300 |
| 2007/0078348 A1 | | 4/2007 | Holman |
| 2009/0156900 A1 | | 6/2009 | Robertson |

(Continued)

FOREIGN PATENT DOCUMENTS

JP     2017-500550 A     1/2017

OTHER PUBLICATIONS

Krafft C, Steiner G, Beleites C, Salzer R. Disease recognition by infrared and Raman spectroscopy. Journal of biophotonics. Feb. 2009;2(1-2):13-28. (Year: 2009).*

*Primary Examiner* — Clifford Hilaire
(74) *Attorney, Agent, or Firm* — DLA Piper LLP (US)

(57) ABSTRACT

Systems and methods for the detection of calculi in the biliary system are disclosed. The systems include an illumination source, one or more filters that filter a first set of illumination photons and a second set of illumination photons, as well as associated processors and detectors. The system is also designed to generate image data sets and generated information related to the location of the calculi.

12 Claims, 22 Drawing Sheets

(56) References Cited

U.S. PATENT DOCUMENTS

| | | |
|---|---|---|
| 2009/0221922 A1 | 9/2009 | Lec et al. |
| 2011/0001061 A1 | 1/2011 | Ishihara |
| 2012/0083678 A1 | 4/2012 | Drauch et al. |
| 2013/0176568 A1 | 7/2013 | Priore et al. |
| 2014/0198315 A1* | 7/2014 | Priore .................... G01J 3/457 |
| | | 356/416 |
| 2015/0133751 A1 | 5/2015 | Stewart et al. |
| 2015/0257635 A1 | 9/2015 | Kubo et al. |
| 2015/0282749 A1 | 10/2015 | Zand et al. |
| 2017/0249744 A1 | 8/2017 | Wang et al. |
| 2018/0116494 A1 | 5/2018 | Treado et al. |

* cited by examiner

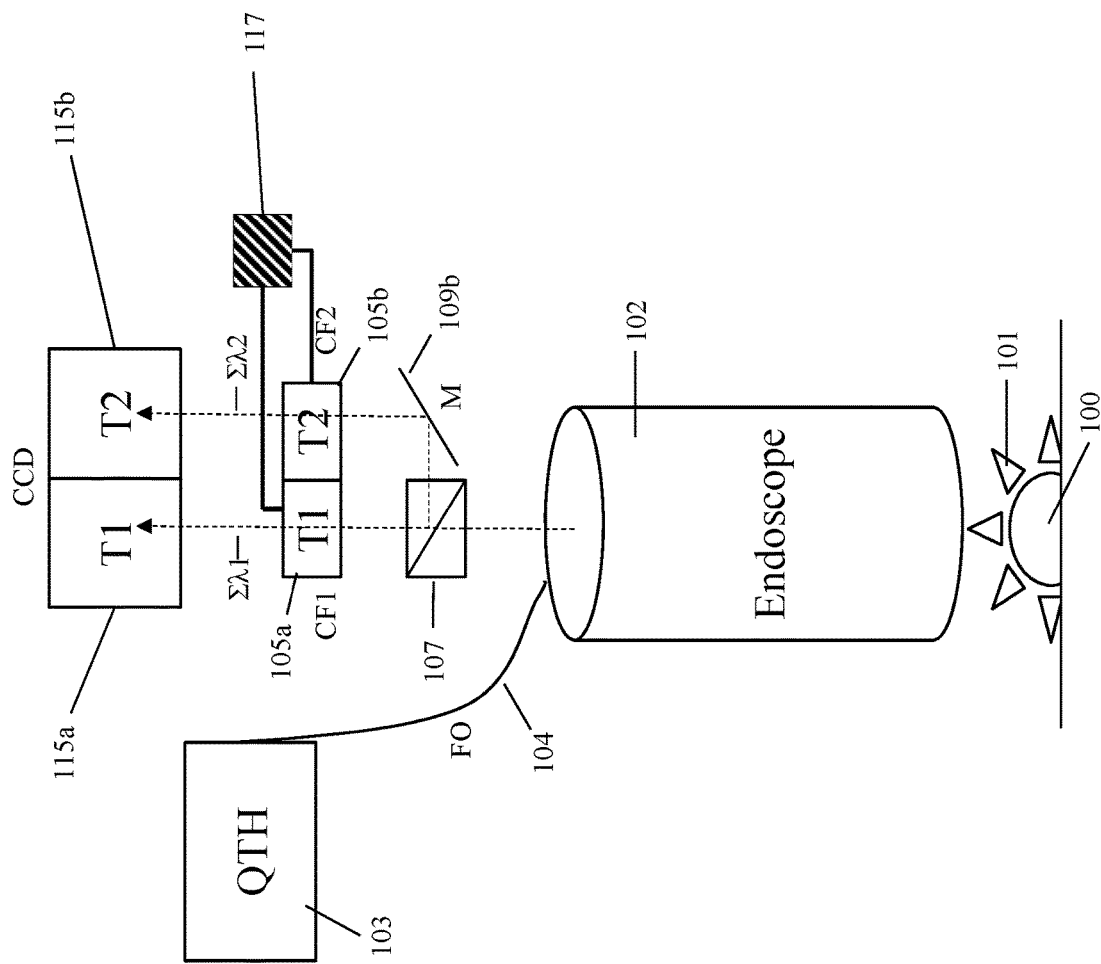
FIG. 1B Patterned CF

DISCRIMINATION OF CALCULI AND TISSUES WITH MOLECULAR CHEMICAL IMAGING

CROSS REFERENCE TO RELATED APPLICATIONS

This application is a continuation of U.S. patent application Ser. No. 16/544,499 filed on Aug. 19, 2019, which claims priority to U.S. Provisional Application Ser. No. 62/719,462, entitled DISCRIMINATION OF CALCULI AND TISSUES WITH MOLECULAR CHEMICAL IMAGING and filed on Aug. 17, 2018, the entireties of which are hereby incorporated by reference.

BACKGROUND

The presence of calculi or stones in the bodies of humans or animals is a common medical condition that causes discomfort and, on occasion, significant pain. The calculi form in various parts of the body where fluids are transported or excreted, including the urinary system, gall bladder and associated biliary system, salivary glands, gastrointestinal tract, and lacrimal passage. Of these, calculi in the gall bladder and associated biliary system are common and pose challenges for treatment. In the United States, approximately 10-15% of the adult population has calculi in the biliary system, with approximately one million cases presenting each year. Gallstone disease is the most costly digestive disease in the United States, with an estimated annual cost of $5 billion. Approximately 20 million people in the United States have gallstones, leading to over one million hospitalizations and 700,000 operative procedures per year. Gallstones are present in approximately 6.5% of men and 10.5% of women, and the prevalence of gallstones increases with age.

Calculi that form in the gall bladder and associated biliary system are formed of various materials depending on the diet, genetics, and other factors of the patient. Typically, the compounds include cholesterol, bile salts, and bilirubin that are excreted by the liver and form bile. If a calculus or calculi grow large enough to block the bile ducts, significant pain results. If the problem persists and is severe enough, the conventional treatment of choice is laparoscopic cholecystectomy, the surgical removal of the gallbladder via a small incision in the abdomen with the aid of a camera. Although this technique has been improved by technological advances, it is still difficult and occasionally results in "conversion" from the minimally invasive laparoscopic procedure to a more invasive open surgical procedure. Problems occur due to non-visualization of the gallbladder, inflamed gallbladder, peri-pancreatic fluid, presence of multiple calculi, cirrhosis of the liver, intraperitoneal adhesions, and ductal anomalies. The removal of calculi from other systems leads to complications as well. For example, the removal of salivary gland calculi sometimes results in unintended facial nerve damage.

Techniques used to locate and remove calculi also cause problems. Radiological studies such as endoscopic retrograde cholangiopancreatography (ERCP) are commonly used to locate calculi in the biliary system but are invasive, time-consuming, and require the use of contrast-enhancing agents. The contrast-enhancing agents often are objectionable to patients and can even be toxic or cause allergic reactions. Complications such as pancreatitis, hemorrhage, perforation, and infection can result. Studies such as magnetic resonance cholangiopancreatography (MRCP) have garnered interest, but while less invasive, they are still expensive and time-consuming and require the use of contrast-enhancing agents.

As such, a need exists for systems and methods for real-time detection of critical anatomical structures and calculi in the body during surgery without the use of contrast-enhancing agents. Such systems and methods would allow surgeons to detect critical anatomical structures and calculi that are otherwise difficult to locate, such as when obscured by tissue, fat, blood, or combinations of those, thus decreasing surgical complications and the need for additional surgeries and procedures.

SUMMARY

The instant disclosure describes medical imaging systems. The medical imaging systems may be used in conjunction with an endoscope. Generally, the medical imaging system includes an illumination source configured to generate illuminating photons. The illuminating photons are transmitted to one or more filters configured to filter a first plurality of illuminating photons and generate a first plurality of filtered photons comprising a first passband wavelength and a second plurality of filtered photons comprising a second passband wavelength. A sample is then illuminated with the first plurality of filtered photons and the second plurality of filtered photons to generate a first plurality of interacted photons and a second plurality of interacted photons, respectively. One or more detectors are configured to detect the first plurality of interacted photons and the second plurality of interacted photons and generate one or more image data sets.

In another embodiment, the imaging system includes an illumination source configured to illuminate a sample and generate interacted photons. One or more filters are configured to filter one or more of a first plurality of the interacted photons and transmit a first passband wavelength and a second plurality of the interacted photons and transmit a second passband wavelength. The first and second passband wavelengths are transmitted to one or more detectors configured to detect the first passband wavelength and the second passband wavelength and generate one or more image data sets.

In yet another embodiment, the imaging system features an illumination source configured to illuminate a sample with one or more of a first plurality of illuminating photons having a first wavelength to generate a first plurality of interacted photons and a second plurality of illuminating photons having a second wavelength to generate a second plurality of interacted photons. One or more detectors are configured to detect the first plurality of interacted photons and the second plurality of interacted photons to generate one or more image data sets.

In some embodiments, the disclosure employs imaging systems of U.S. Patent Application Publication Number 2018/0116494, filed as application Ser. No. 15/374,769 on Dec. 9, 2016 to Treado et al. and entitled MOLECULAR CHEMICAL IMAGING ENDOSCOPIC IMAGING, assigned to ChemImage Corporation, Pittsburgh, PA, the entirety of which is incorporated by reference herein.

BRIEF DESCRIPTION OF THE DRAWINGS

FIG. 1B illustrates a patterned conformal filter configuration with a CCD detector according to an embodiment.

DETAILED DESCRIPTION

Figure 1:
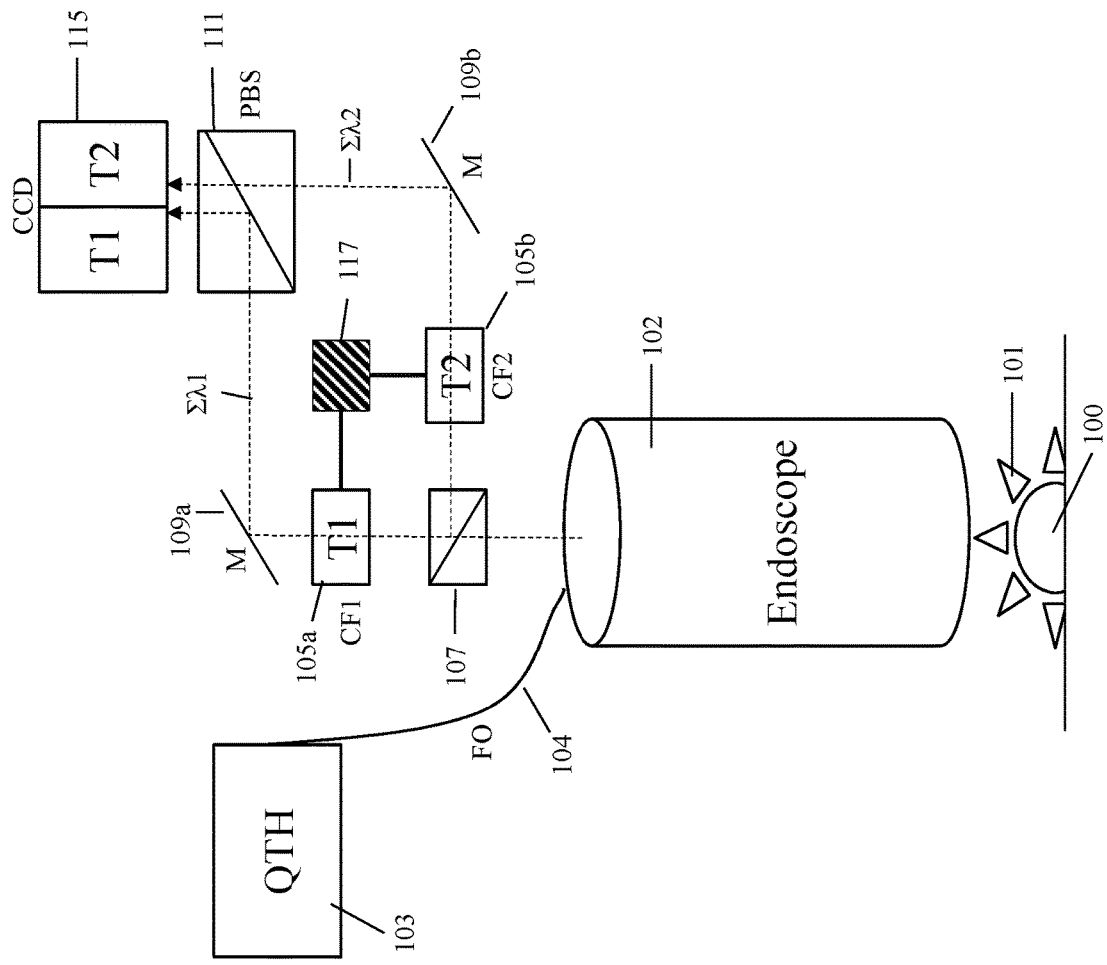
FIG. 1 illustrates an endoscope comprising an imaging system having a plurality of conformal filters in a dual polarization configuration according to an embodiment.

The present disclosure features intraoperative medical imaging systems which can assist surgeons in various medical procedures. The systems disclosed herein are suitable for use as stand-alone devices or may be incorporated into other medical imaging devices such as a robotic platform. In one embodiment, the systems disclosed herein may be used in conjunction with an endoscope. The medical imaging systems disclosed herein may provide real-time and/or near real-time detection of calculi (stones) or biliary ducts and/or other critical anatomical structures or other nearby tissue during surgical, endoscopic, diagnostic procedures. Generally, the systems disclosed herein provide illuminating a biological sample, collecting photons that have interacted with the sample, detecting the interacted photons to generate an image data set of the sample, and analyzing the image data set. Interacted photons may comprise one or more of photons absorbed by a sample, photons reflected by a sample, photons scattered by a sample, and photons emitted by a sample. In one embodiment, the medical imaging system provides multivariate imaging. Multivariate imaging features generating two or more wavelengths corresponding to a first image data set (T1) and a second image data set (T2). These first and second image data sets may be analyzed using an optical computation. Multivariate imaging creates enhanced image contrast and increased discrimination between a target and background. In certain embodiments, the first image data set and the second image data set feature hyperspectral image data. In another embodiment, the medical imaging systems feature imaging frame rates of >10 Hz (frames/second).

The systems disclosed herein may be used on various biological samples, such as calculi, tissues, organs, anatomical structures, physiological systems, cells, blood, fat, nerves, muscle and the like. In certain embodiments, the systems may be employed in various areas of the body, which would be apparent to one of skill in the art in view of this disclosure. For example, the systems might be employed to investigate and/or perform surgery in the gall bladder and associated biliary system, urinary system, gastrointestinal tract, mouth and salivary glands, lacrimal passage, and the like. In such an application, the systems may be employed in any of the esophagus, the stomach, the duodenum, the small intestine, the large intestine/colon, the bile duct, the rectum, the anus and the like. The systems may further be employed on structures of the respiratory tract including, without limitation, the nose, the sinuses and the lower respiratory tract. In other embodiments, the systems disclosed herein may be used to investigate and/or perform surgery on structures comprising the urinary tract, such as the bladder, ureter, kidneys and so forth. In yet other embodiments, the systems may be employed on structures comprising the female reproductive system, such as the cervix, uterus, fallopian tubes and the like. Further, the systems may be employed in medical procedures performed during pregnancy, such as to investigate and/or perform medical procedures on the amnion and fetus. In another embodiment, the systems described herein may be employed to investigate and/or perform surgery on the structures involving the musculoskeletal system, i.e., orthopaedics, including the structures of the hand, the knee, the elbow, the shoulder, the spine, including the epidural cavity, bursae, muscles, ligaments, connective tissues and the like.

Further, the systems may be configured to discriminate between two or more different biological samples. For example, the systems disclosed herein may be configured to discriminate between a calculus and surrounding tissues of the gall bladder, bile ducts, liver, pancreas, and other components of the biliary system. In other embodiments, the systems are configured to discriminate between a calculus and the bladder, ureter, kidneys, and other components of the urinary tract. In other embodiments, the systems are configured to discriminate between a calculus and the tissues in the mouth. In other embodiments, the systems are configured to discriminate between a calculus and the tissues of the circulatory system. In other embodiments, the systems are configured to discriminate between different kinds of tissue, for example, between ducts and surrounding tissues.

As disclosed herein, the systems of the present disclosure provide illumination to tissues in the body. It is known that such illumination may penetrate a biological sample up to several centimeters, depending on wavelength and tissue type. Thus, such illumination penetration permits the imaging of bodily fluids contained inside an anatomical structure. This is especially useful in the detection of calculi, which may be contained within organs or other tissues of the body such as bile ducts, ureters, bladders, kidneys, and similar structures.

As was noted above, contrast-enhancing agents suitable for prior art imaging techniques based on x-rays or magnetic resonance are often objectionable, toxic, or cause allergic reactions. Thus, some embodiments of the disclosure are contemplated as completely omitting the use of contrast-enhancing agents, that is, the systems operate without the use of contrast-enhancing agents, and methods omit any steps adding a contrast-enhancing agent.

In other embodiments, however, there may be a desire to include a contrast-enhancing agent. In those embodiments, contrast-enhancing agents may include one or more stains or dyes. When only one stain or dye is used, the procedure is referred to as staining. Multiple staining comprises the use of more than one stain or dye. As used herein, a "stain" or "dye" is any chemical or biological compound that can bind to a substance in a biological sample, to induce a color and may include dyes attached to antibodies or antibody-like molecules having a specific affinity for a particular tissue type, such as cancerous tissue or organs. For example, a stain or dye can bind to a particular cellular or biochemical structure (e.g., cell membrane, organelles, nucleic acid, protein) to induce contrasts when viewed using the systems described herein. In some embodiments, the stain or dye can induce a color by emitting electromagnetic radiation at one or more wavelengths when excited (i.e., fluoresce). It is contemplated that because the contrast-enhancing agents contemplated by the disclosure do not need to interact with x-rays or magnetic resonance imagery, they can be made safe, non-toxic, and less objectionable to patients than prior art contrast-enhancing agents.

The one or more stains or dyes can be used, for example, in vivo or ex vivo. In some embodiments, the stain or dye is any stain or dye suitable for use in a living organism/individual that does not kill cells, i.e., a biological stain. Examples of biological stains include, but are not limited to, azo dyes, arylmethane dyes, cyanine dyes, thiazine dyes, xanthene dyes (e.g., eosin), natural stains (e.g., alizarin red), steroids, trypan blue, janus green, indocyanine green, alizarin red, propidium iodide, erythrosine, 7-aminotinomycin D, and Nile blue. In one embodiment, the contrasting-enhancing agent is a fluorescent contrast-enhancing agent. In one embodiment, the contrast-enhancing agent may include a flourophor. Suitable fluorophores include an immuno-fluorescent compound, a basophilic compound, an acidophilic compound, neutral stains and naturally occurring luminescent molecules.

When one or more stains or dyes are used in conjunction with the systems and methods described herein, a user (e.g., a surgeon) can intra-operatively identify histology, pathology, morphology, position, chemicals, and chemical reactions in or around the biological sample. For example, some (one or more) biological stains can identify cancerous cells so that the surgeon can resect the tumor. Other biological stains can also identify living cells (tissue) versus non-living cells. Once the contrast-enhancing agent is applied to the biological sample, the sample can be irradiated with photons having a wavelength within the illumination wavelength range of the applied contrast-enhancing agent in order to obtain spectral images as set forth in the instant disclosure.

In another embodiment, the contrast-enhancing agent may be ingested by a subject, where the contrast-enhancing agent will appear in a bodily fluid. In one embodiment, the contrast-enhancing agent may be taken orally, through an IV, applied to a local site or sample, or through other means as would be apparent to one of skill in the art in view of this disclosure. Once the contrast-enhancing agent is ingested, the target biological sample may be examined by the systems disclosed herein. The systems may be configured to detect the contrast-enhancing agent in the bodily fluid to provide contrast between structures comprising the bodily fluid and surrounding biological samples, such as surrounding tissue. For example, a patient may orally ingest a solution comprising a contrast-enhancing agent where the contrast-enhancing agent at a certain time thereafter appears in the patient's urine. An endoscopic procedure may be performed on the kidney area of the patient with a system according to the instant disclosure. The system is configured to detect the contrast-enhancing agent present in the urine located in an ureter to differentiate the ureter and other surrounding tissues.

In another embodiment, a biological tissue may be imaged with a system according to the instant disclosure ex vivo. In such an application, the biological sample may be removed and analyzed outside of the surgical site. Traditional staining methods may be applied to the resected tissue to determine one or more biological characteristics of the sample. Ex vivo techniques are known in the art and would be apparent to one of skill in the art in view of this disclosure.

In another embodiment, the biological sample may be enhanced by applying a completely electronic and reagent-less digital stain to the sample. Digital stains are applied to an image data set by using an algorithm. The use of a digital stain eliminates the need to apply a physical and/or chemical stain to the biological sample. Digital stains may be applied to any of the image data sets obtained through the systems disclosed herein. One example of the application of a digital stain to a Raman data set may be found in U.S. Patent Application Publication Number 2012/0083678, filed as application Ser. No. 13/200,779 on Sep. 30, 2011 to Drauch et al. and entitled SYSTEM AND METHOD FOR RAMAN CHEMICAL ANALYSIS OF LUNG CANCER WITH DIGITAL STAINING, assigned to ChemImage Corporation, Pittsburgh, PA, the entirety of which is incorporated herein by reference. The digital stain may be used alone without the inclusion of a contrast-enhancing agent, or it may be used in conjunction with a contrast-enhancing agent.

In some embodiments, the system is in the form of an endoscope, laparascope, or surgical microscope that can be used for diagnostics or surgery. In other embodiments, the system is in the form of a stationary or semi-mobile imaging platform used in the operating theater. Other medical imaging instrumentation and the detection of other types of biological samples is further contemplated by the instant disclosure and would be apparent to those of skill in the art in view of the instant disclosure.

The medical imaging instruments disclosed herein provide real-time multivariate imaging by generating a multivariate signal using one or more detectors. The detectors detect the multivariate signal to produce one or more image data sets. Provided herein are two ways to achieve this result. One such method includes illuminating a sample, collecting interacted photons that have interacted with the sample, and modulating the collected signal prior to passing the signal on to a detector. A second method includes modulating the illumination source signal prior to interaction with a sample, collecting interacted photons of the modulated signal, and detecting the interacted photons of the signal. Both processes provide a modulated signal to produce a multivariate chemical image in real-time with enhanced contrast to assist surgeons with removing calculi from surrounding tissue. The embodiments contained herein can further be configured to provide real-time images displayed in stereo vision. Such a configuration would be apparent to those of skill in the art in view of this disclosure. Stereo vision further assists a surgeon by providing the depth perception needed in medical procedures employing medical imaging techniques, such as in endoscopic procedures. Stereo vision techniques for endoscopic, laproscopic, and open surgical procedures are contemplated as they improve the accuracy and effectiveness of the procedures. Systems and methods recited herein provide exemplary embodiments of the instant disclosure and are not intended to limit the disclosure to any particular embodiment. Real-time vision permits surgeons to have their perspective of the procedure improved without delay and allows them to observe the effect of their instruments and actions instantly within the body and during the procedure.

Because the systems and methods of the present disclosure provide enhanced contrast and improved imaging, often in real time, they are especially suited for medical diagnostics and the operating theater. In some embodiments, the systems are employed during surgery or other medical procedures to remove calculi from humans or animals. Such procedures include but are not limited to open surgical procedures and laparoscopic procedures. The use of the disclosed systems and methods may be employed during the removal of calculi from the mouth and saliva glands, biliary tract, urinary tract, or any other region of the body described herein. In some embodiments, the systems and methods are useful to distinguish between critical tissues, such as ducts, biliary ducts, vasculature, veins, organs, nerves, and the like, and surrounding tissues such as muscle, fat, and the like.

In still further embodiments, the systems and methods of the present disclosure may provide multi-target analysis of a sample. The ability to analyze multiple targets is especially useful in procedures such as those discussed above because it enables surgeons and medical staff to identify not just the location of calculi with respect to other tissue, but also to identify the different types of tissue. For example, the systems and methods of the invention may be able to identify and distinguish between calculi, ducts, and surrounding tissue. In other embodiments, the systems and methods may be able to identify and distinguish between calculi, ducts, and surrounding organs. In other embodiments, the systems and methods may be able to identify and distinguish between calculi, ducts, and surrounding vasculature. The systems and methods of the disclosure may be used to identify and distinguish between ducts and surrounding tissue even when no calculi are present.

Multi-target tuning is accomplished by using two different tuning states, for instance in sequential scan imaging and conformal imaging, to detect multiple targets at once. In sequential scan imaging, at least two wavelengths are used to detect multiple targets (for example, a bile duct and surrounding tissue and a calculus) at once in a single field of view. In conformal imaging, the conformal filters are tuned to at least two tuning states to detect multiple images or targets at once in the same field of view.

In other embodiments, the imaging is achieved using sequential scan imaging techniques. In such techniques, the system collects multiple discrete wavelength images over time, and each individual image is combined to generate a hypercube. The hypercube contains individual pixels, and each individual pixel contains at least two values that correspond to the individual image spectra that were collected. For example, a sequential scan filter may collect two discrete wavelengths, generate a hypercube where each pixel contains two intensity values corresponding to the wavelengths, and process the hypercube to form a score image that depicts those intensity values. This example is not intended to be limiting and it is contemplated that there may be any number of additional wavelengths depending on the application.

In other embodiments, the imaging is achieved using conformal imaging, which simultaneously (i.e., in a single acquisition) collects a range of wavelengths, such as multiple passbands, and processes them from the hypercube. Again, this example is not intended to be limiting and any number of wavelength combinations may be utilized, along with any combination of targets to be detected.

Modulating Collected Optical Signal

The following embodiment features modulating an optical signal after the collection of photons that have interacted with a sample.

System Having Conformal Filters in a Dual Polarization Arrangement

Referring now to FIG. 1, a biological sample 100 may be illuminated and/or excited by an illumination source 103. In one embodiment, the illumination source 103 may comprise a quartz tungsten halogen light source. In other embodiments, the illumination source 103 may comprise a metal halide light source, a light emitting diode (LED), a LED array having a uniform selection of emitters which emit over a constant wavelength range or a plurality of emitters which emit over a diversity of wavelength ranges, a pulsed LED, a pulsed LED array, a laser, a pulsed laser, a broadband illumination source, gas discharge light source, a fluorescent light source, an arc light source, a xenon arc lamp source, an LED light source in combination with phosphors and/or quantum dots, and the like and combinations thereof. The illumination sources 103 are selected depending on the wavelengths of interest for analysis and the physical footprint available for the light source, among other factors. Of the above, the lasers and/or LED light sources may be selected depending on the wavelengths of interest. The lasers may be gas discharge or solid state or semiconductor lasers and include helium-neon, argon, krypton, xenon ion, nitrogen, carbon monoxide, eximer, dye lasers such as stilbene, coumarin, and rhodamine, solid state or semiconductor lasers such as ruby, Nd:YAG, NdCrYAG, Nd:YLF, Nd:YVO$_4$, Nd:YCa$_4$O$_4$, Nd:YCa$_4$O(BO$_3$)$_3$, Nd:glass, Ti:sapphire, Tm:YAG, Tb:YAG, Yb doped glass, Ho:YAG, Cr:ZnSe, Ce:LiSAF, Ce:LiCAF, GaN, InGaN, AlGaInP, AlGaAs, InGaAsP, and lead salt, vertical cavity surface emitting lasers, quantum cascade laser, and hybrid silicon lasers. The illumination source may have a fixed spectral emission or may be tunable by combining sources, filtering, and/or modulating the sources and/or filters. Depending on the size, thermal output, power requirements, and so forth, the illumination source may be used directly within an endoscope or in a system, or remotely via optical fibers that are transparent to the desired wavelengths. The illumination source 103 generates illuminating photons that are directed from the illumination source 103 to the distal end of an endoscope 102 through a fiber optic bundle 104. The endoscope 102 is configured to direct interacted photons 101 that have interacted with the biological sample 100 to a polarizing beam splitter 107. Two independently tunable conformal filters 105a, 105b are situated along distinct orthogonal beam paths to filter orthogonal polarization components emerging from polarizing beam splitter 107. Suitable conformal filters for use in the instant disclosure may include those disclosed in U.S. Patent Application Publication Number 2013/0176568 to Priore et al., filed Jan. 4, 2013, assigned to ChemImage Corporation and entitled CONFORMAL FILTER AND METHOD OF USE THEREOF, the entirety of which is incorporated by reference herein.

In this arrangement, the paths of the filtered beams are not parallel through the conformal filters 105a, 105b, but are directed by appropriate reflectors, i.e., mirrors, 109a, 109b to a beam combiner 111. In alternate embodiments, the beam combiner may be a polarizing cube or polarizing beam splitter. In another embodiment, the orthogonal components may comprise the same or different multi-passband wavelengths $\Sigma\lambda_1$ and $\Sigma\lambda_2$. In the exemplary embodiment, the conformal filter 105a is configured to generate polarized multi-passband wavelengths $\Sigma\lambda_1$, and conformal filter 105b is configured to generate polarized multi-passband wavelengths $\Sigma\lambda_2$. In the exemplary embodiment, multi-passband wavelengths $\Sigma\lambda_1$ and $\Sigma\lambda_2$ are directed to a detector 115 through a lens assembly (not shown). In another embodiment, the multi-passband wavelengths $\Sigma\lambda_1$ and $\Sigma\lambda_2$ may be combined as they are directed to the detector 115. In some embodiments, beam paths from the polarizing beam splitter 107 to the beam combiner 111 may be made symmetrical to avoid, for example, a need for infinitely-corrected optics.

The detector 115 as illustrated comprises a CCD detector. However, the present disclosure contemplates that the detector 115 may comprise other suitable detectors including, for example, a complementary metal-oxide-semiconductor (CMOS) detector, an indium gallium arsenide (InGaAs) detector, a platinum silicide (PtSi) detector, an indium antimonide (InSb) detector, a mercury cadmium telluride (HgCdTe) detector, or combinations thereof. The detectors 115 are selected depending on the desired spectra to be analyzed. The spectra may include light or radiation that is in the range of ultraviolet (UV-A, UV-B, and/or UV-C) to short wave infrared (SWIR), and further includes near infrared (NIR) and visible light. Still referring to FIG. 1, the two conformal filters 105a and 105b may be tuned in unison to the same multi-passband wavelengths ($\Sigma\lambda_1 = \Sigma\lambda_2$) using an controller 117. In another embodiment, the controller 117 may be configured to independently tune each multi-passband wavelength $\Sigma\lambda_1$ and $\Sigma\lambda_2$ to respectively process orthogonal components of the input. Therefore, by appropriate control, the conformal filters 105a and 105b may be tuned to the same multi-passband wavelengths or to two different multi-passband wavelengths ($\Sigma\lambda_1 \neq \Sigma\lambda_2$) at the same time. The controller 117 may be programmable or software-implemented to allow a user to selectively tune each conformal filter as desired. In the embodiment of FIG. 1, a fast switching mechanism (not shown) may be provided to switch between the two views (or spectral images) corresponding to spectral data collected by the detector 115 from each of the conformal filters 105a and 105b. Alternatively, two such spectral views or images may be combined or overlaid into a single image to increase contrast or intensity or for the purpose of comparison. The exemplary embodiment in FIG. 1 comprises a single CCD detector 115 to capture the filtered signals received from the conformal filters 105a and 105b.

FIG. 1B illustrates an alternative embodiment of the instant disclosure. In this embodiment, the beam combiner 111 and mirror 109a may be removed, and two detectors may be used. The first conformal filter 105a is configured to filter and transmit first multi-passband wavelengths corresponding to a T1 state to a first detector 115a where the first detector detects the first multi-passband wavelengths and generates a first image data set (T1). In similar fashion, the second conformal filter 105b is configured to filter and transmit second multi-passband wavelengths corresponding to a T2 state to a second detector 115b where the second detector 115b detects the second multi-passband wavelengths and generates a second image data set (T2).

U.S. Patent Application Publication Number 2014/0198315 to Treado et al., filed Jan. 15, 2014 assigned to ChemImage Corporation and entitled SYSTEM AND METHOD FOR ASSESSING ANALYTES USING CONFORMAL FILTERS AND DUAL POLARIZATION discloses the use of conformal filters in a dual polarization configuration as discussed above and is incorporated by reference herein in its entirety.

Figure 1A:
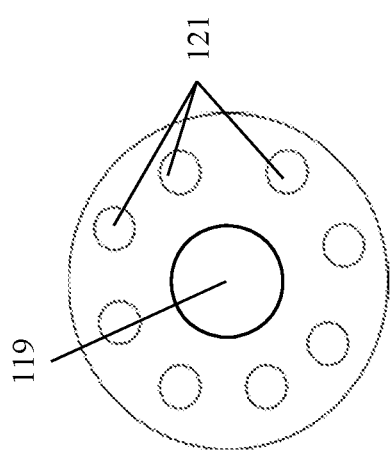
FIG. 1A is an end-on view of the endoscope according to the embodiment in FIG. 1.
Figure 2:
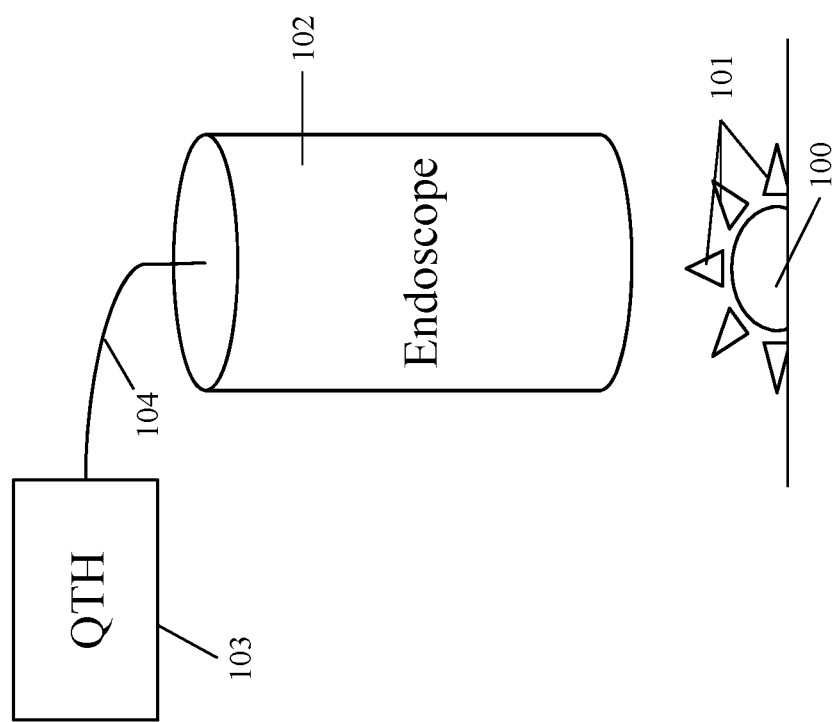
FIG. 2 illustrates an endoscope comprising an imaging system having a plurality of multivariate optical element (MOE) filters according to an embodiment.
Figure 2A:
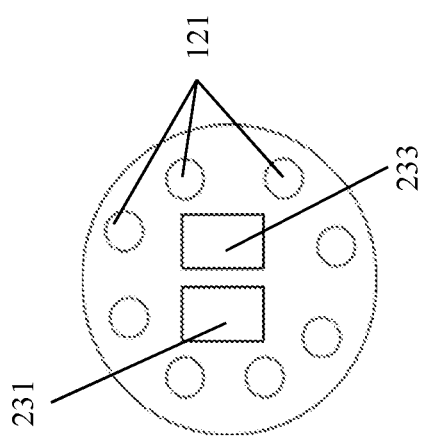
FIG. 2A is an end-on view of the endoscope according to the embodiment in FIG. 2.
Figure 2B:
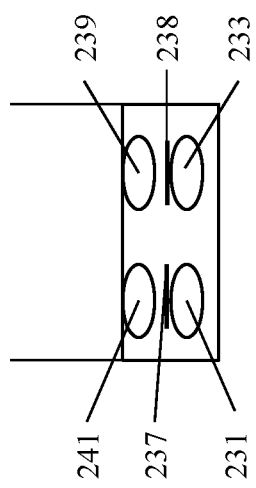
FIG. 2B is a cross-sectional view of the distal end of the endoscope according to the embodiment in FIG. 2.

FIG. 1A illustrates an end-on view of the distal end of the endoscope 102. The distal end features a lens 119 for collecting interacted photons 101 and fiber ends 121 of the fiber optic bundle 103 which illuminate the biological sample 100 to generate the interacted photons 101. The detector 115 detects the multi-passband wavelength from the conformal filters 105a and 105b and is configured to generate one or more image data sets. The image data set may comprise a T1 image corresponding to the first multi-passband wavelengths $\Sigma\lambda_1$ and a T2 image corresponding to the second multi-passband wavelengths $\Sigma\lambda_2$. In one embodiment, the image data set comprises a Raman image data set. The one or more image data sets generated by the detector 115 may be further analyzed as set forth below System Having Multivariate Optical Element (MOE) Filter Arrangements FIG. 2 illustrates another embodiment featuring modulating the collected optical signal. In FIG. 2, an illumination source 103 generates illuminating photons which traverse along a fiber optic bundle 104 through an endoscope 102 and terminate at a series of fiber ends 121 on the distal end of the endoscope 102 (shown in FIG. 2A). The fiber ends 121 emit illuminating photons to illuminate a sample 100 to produce a plurality of interacted photons 101. The interacted photons 101 are collected by a first collection optic 231 and a second collection optic 233. The first collection optic 231 collects a first portion of the interacted photons 101 and passes these photons on to a first Multivariate Optical Element (MOE) filter 237 (shown in FIG. 2B) which filters the first portion of the interacted photons 101 to generate a first portion of filtered photons. The first portion of filtered photons is detected by a first detector 241. Further, the second collection optic 233 collects a second portion of the interacted photons 101 and passes these photons on to a second MOE filter 238 to generate a second portion of filtered photons. The second portion of filtered photons is detected by a second detector 239. In one embodiment, the first detector 241 and the second detector 239 are charge coupled device (CCD) detectors comprised of Si or other materials. In other embodiments, the detectors 239 and 241 may comprise other suitable detectors including, for example, a complementary metal-oxide-semiconductor (CMOS) detector, a detector of Si or other materials, a Si quantum dot detector, an indium gallium arsenide (InGaAs) detector, a platinum silicide (PtSi) detector, an indium antimonide (InSb) detector, a mercury cadmium telluride ("HgCdTe") detector, a silicon germanium detector (SiGe), or combinations thereof.

In one embodiment, the first MOE filter 237 may be configured to generate a first filtered passband. In one embodiment, the first MOE filter 237 is configured to generate a first filtered passband consistent with a randomized target or background. In one embodiment, the second MOE filter 238 may be configured to generate a second filtered passband consistent with the target or sample 100. In embodiments where the first MOE filter 237 is configured to generate a first filtered passband corresponding to a randomized target or background, the second MOE filter 238 may be configured to generate a second filtered passband corresponding to a target or sample. This type of embodiment permits discrimination of both a target and a background.

An MOE features wide-band, optical interference filters encoded with an application-specific regression (or pattern) specific to a target. MOEs provide multivariate optical computing by performing the optical computation based on the pattern of the filter. In other words, MOEs are uniquely tuned to the pattern that needs to be measured using multivariate analysis on the filter as opposed to capturing multiple measurements at different wavelengths to estimate the full spectrum of a target and processing this information by applying multivariate statistics to the spectrum. Thus, MOEs increase throughput and efficiency over conventional filters, which can increase the speed of analysis.

The first detector 241 is configured to detect the first filtered passband from the first MOE filter 237 to generate a first image data set (T1), and the second detector 239 is configured to detect the second filtered passband from the second MOE filter 238 to generate a second image data set (T2). The first image data set and the second image data set may be further analyzed, as set forth below.

Modulating Illumination Source Signal

The following embodiments feature modulating the illumination source signal prior to interaction with a sample. As above, the illumination source 103 may comprise a quartz tungsten halogen light source. In other embodiments, the illumination source 103 may comprise a metal halide light source, a light emitting diode (LED), a LED array having a uniform selection of emitters which emit over a constant wavelength range or a plurality of emitters which emit over a diversity of wavelength ranges, a pulsed LED, a pulsed LED array, a laser, a pulsed laser, a broadband illumination source, gas discharge light source, a fluorescent light source, an arc light source, a xenon arc lamp source, an LED light source in combination with phosphors and/or quantum dots, and the like and combinations thereof. The illumination sources 103 are selected depending on the wavelengths of interest for analysis and the physical footprint available for the light source, among other factors. Of the above, the lasers and/or LED light sources may be selected depending on the wavelengths of interest. The lasers may be gas discharge or solid state or semiconductor lasers and include helium-neon, argon, krypton, xenon ion, nitrogen, carbon monoxide, eximer, dye lasers such as stilbene, coumarin, and rhodamine, solid state or semiconductor lasers such as ruby, Nd:YAG, NdCrYAG, Nd:YLF, Nd:YVO$_4$, Nd:YCa$_4$O$_4$, Nd:YCa$_4$O(BO$_3$)$_3$, Nd:glass, Ti:sapphire, Tm:YAG, Tb:YAG, Yb doped glass, Ho:YAG, Cr:ZnSe, Ce:LiSAF, Ce:LiCAF, GaN, InGaN, AlGaInP, AlGaAs, InGaAsP, and lead salt, vertical cavity surface emitting lasers, quantum cascade laser, and hybrid silicon lasers. The illumination source may have a fixed spectral emission or may be tunable by combining sources, filtering, and/or modulating the sources and/or filters. Depending on the size, thermal output, power requirements, and so forth, the illumination source may be used directly within an endoscope or in a system, or remotely via optical fibers that are transparent to the desired wavelengths.

System Having a Conformal Filter Arrangement

Figure 3:
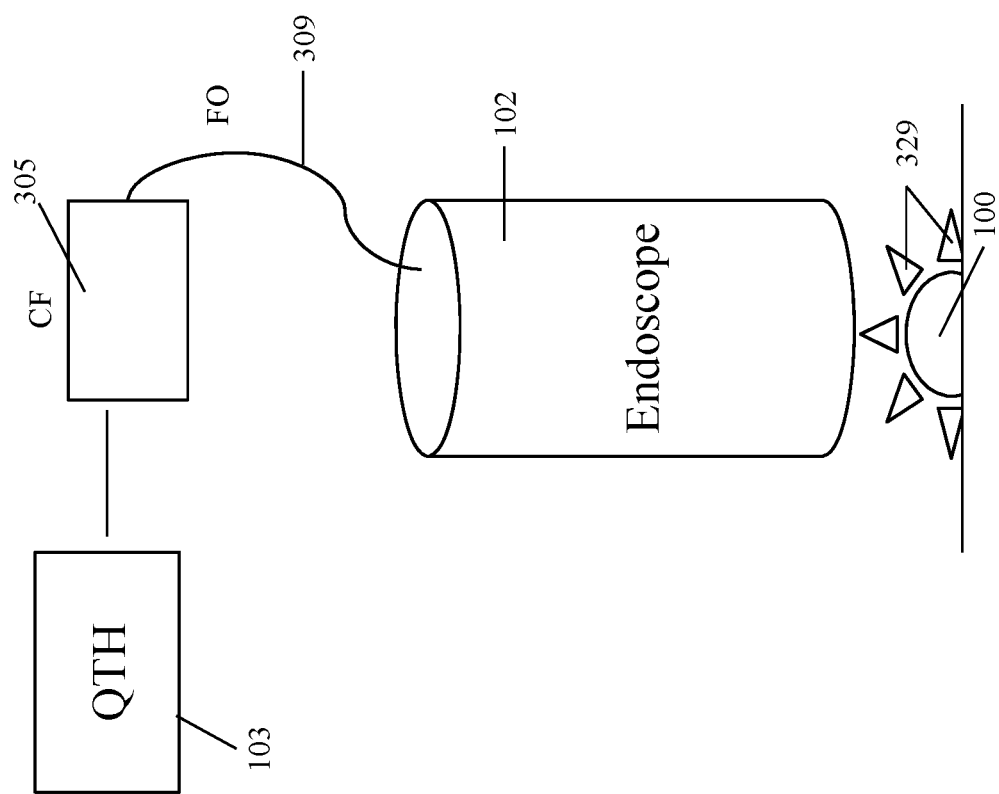
FIG. 3 illustrates an endoscope comprising an imaging system having a conformal filter according to an embodiment.
Figure 3A:
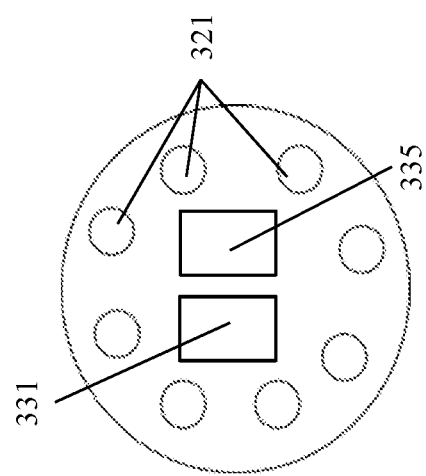
FIG. 3A is an end-on view of the endoscope according to the embodiment in FIG. 3.

FIG. 3 illustrates an illumination source 103 configured to generate illuminating photons which are transmitted through a filter 305. In one embodiment, the filter 305 comprises a conformal filter, as disclosed herein. In another embodiment, the filter 305 may comprise other filters, such as a liquid crystal tunable filter (LCTF), or filters as would be apparent to those of skill in the art in view of this disclosure. In one embodiment, the filter 305 may include a multi-conjugate filter. The filter 305 is controlled by a controller (not shown) that is configured to switch the filter configuration to pass first multi-passband wavelengths ($\Sigma\lambda_1$) and subsequently be switched to configure the filter to pass second multi-passband wavelengths ($\Sigma\lambda_2$). In one embodiment, the rate at which the controller switches between the two states is on a millisecond order of magnitude. The filter 305 transmits each multi-passband wavelength, $\Sigma\lambda_1$ and $\Sigma\lambda_2$, through a fiber optic bundle 309 to the distal end of an endoscope 102 where each multi-passband wavelength exits the distal end of the endoscope 102 via fiber ends 321, as shown in FIG. 3A, to illuminate the sample 100 and produce interacted photons 329. The interacted photons 329 are collected by a first detector 331 and a second detector 335 located on the distal end of the endoscope 102. The detectors 331 and 335 of the illustrated embodiment comprise CCD detectors. However, other detectors, such as those disclosed herein, may be employed. The first detector 331 may be configured to detect substantially only the first multi-passband wavelengths. In one embodiment, the first detector 331 may be timed, i.e., turned off and on, to detect the first multi-passband wavelengths concurrent with the filter 305 transmitting the first multi-passband wavelengths. Likewise, the second detector 335 may be configured to detect substantially only the second multi-passband wavelengths. In one embodiment, the second detector 335 may be timed, i.e., turned off and on, to detect the second multi-passband wavelengths concurrent with the filter 305 transmitting the second multi-passband wavelengths. In another embodiment, the timing sequence of the modulation between the first multi-passband wavelengths and the second multi-passband wavelengths and the detection of the first multi-passband wavelengths and the second multi-passband wavelengths with the corresponding detector may be controlled by the controller (not shown). The first detector 331 detects the first multi-passband wavelengths and generates a first image data set (T1), and the second detector 335 detects the second multi-passband wavelengths and generates a second image data set (T2). In one embodiment, the first image data set and the second image data set may be further analyzed as set forth below.

System Having Conformal Filters in Dual Polarization Arrangement

Figure 4:
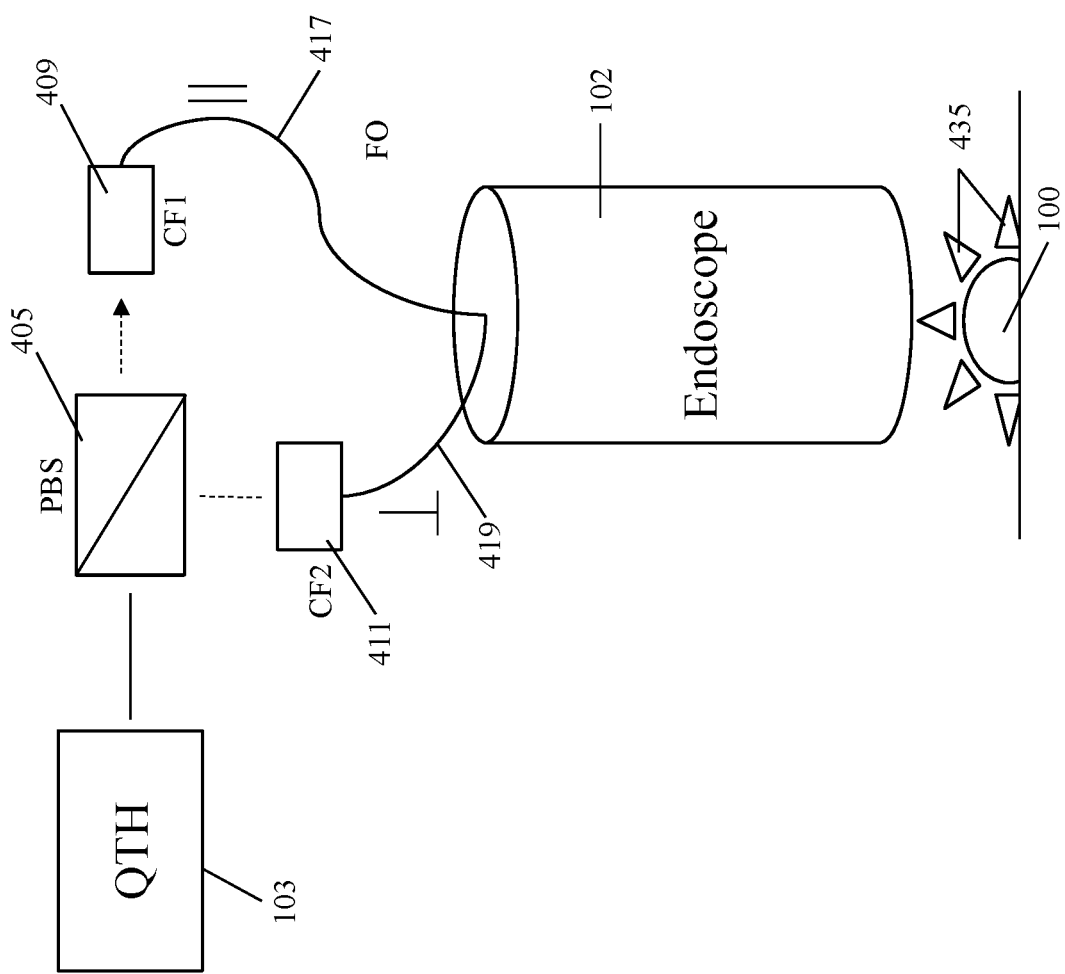
FIG. 4 illustrates an endoscope comprising an imaging system having a plurality of conformal filters in a dual polarization configuration for source illumination modulation according to an embodiment.

FIG. 4 illustrates another embodiment of illumination source modulation. In this embodiment, an illumination source 103 generates an optical signal that is transmitted through a polarizing beam splitter 405 which splits the optical signal into a first polarization signal and a second polarization signal. The first polarization signal is transmitted to a first filter 409, and the second polarization signal is transmitted to a second filter 411. In one embodiment, the first filter 409 and the second filter 411 each comprise a conformal filter, as described herein. In another embodiment, the first filter 409 and second filter 411 each comprise an LCTF. In one embodiment, the first filter 409 and the second filter 411 each may comprise a multi-conjugate filter. The first filter 409 is configured to filter the first polarization signal and transmit first multi-passband wavelengths ($\Sigma\lambda_1$), and the second filter 411 is configured to filter the second polarization signal and transmit second multi-passband wavelengths ($\Sigma\lambda_2$). The first multi-passband wavelengths and the second multi-passband wavelengths are transmitted from their respective filters 409, 411 to the distal end of an endoscope 102 via a first fiber optic bundle 417 and second fiber optic bundle 419, respectively. In one embodiment, the first fiber optic bundle 417 and the second fiber optic bundle 419 comprise a polarization-maintaining fiber optic bundle.

Figure 4A:
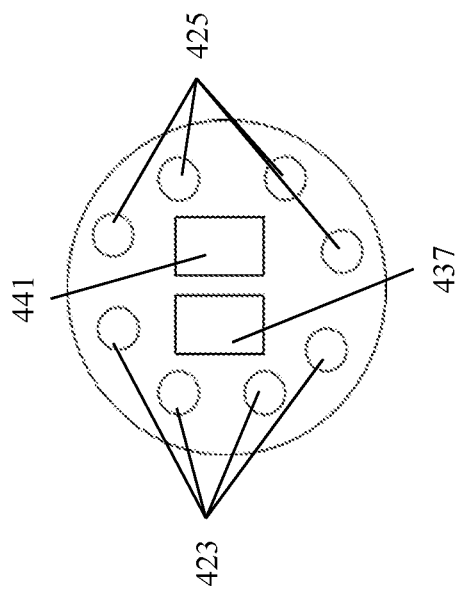
FIG. 4A is an end-on view of the endoscope according to the embodiment in FIG. 4.
Figure 4B:
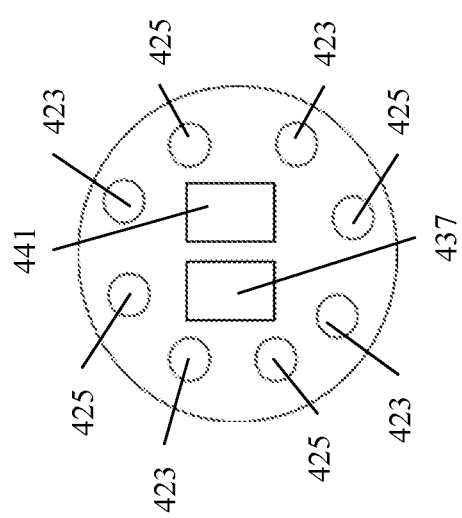
FIG. 4B is an end-on view of an alternate embodiment of the endoscope according to the embodiment in FIG. 4.

FIG. 4A and FIG. 4B illustrate different embodiments of the distal end of the endoscope 102. The first fiber optic bundle 417 and the second fiber optic bundle 419 traverse through the endoscope 102 to the distal end. The first fiber optic bundle 417 terminates at first fiber ends 423, and the second fiber optic bundle 417 terminates at second fiber ends 425. FIG. 4A illustrates one exemplary arrangement of the first fiber ends 423 with respect to the second fiber ends 425. In this embodiment, the first fiber ends 423 are distributed together on one side of the distal end of the endoscope 102 and the second fiber ends 425 are distributed together on the other side of the distal end of the endoscope 102. In FIG. 4B, another embodiment is shown where the first fiber ends 423 and the second fiber ends 425 alternate around the distal end of the endoscope 102. Suitable arrangements of the fiber ends would be apparent to those of skill in the art in view of this disclosure. The sample 100 is illuminated from the multi-first passband wavelengths and the second multi-passband wavelengths emitting from the first fiber ends 423 and the second fiber ends 425, respectively, to generate interacted photons 435. The interacted photons 435 are detected by a first detector 437 and a second detector 441 disposed on the distal end of the endoscope 102. In the illustrated embodiment, the first detector 437 and the second detector 441 are CCD detectors. However, other suitable detectors, such as those disclosed herein, may be employed, and such detectors would be apparent to one of skill in the art in view of this disclosure. In one embodiment, the first fiber optic bundle 417 and the second fiber optic bundle 419 comprise polarization maintaining fiber optic bundles. In such an embodiment, polarizers (not shown) may be disposed in front of the detectors 437 and 441, which are arranged for stereovision, and configured to differentiate between a T1 state and a T2 state on the basis of polarization. In one embodiment, the first detector 437 is configured to detect substantially only interacted photons generated from the first multi-passband wavelengths, and the second detector 441 is configured to detect substantially only interacted photons generated from the second multi-passband wavelengths. As such, the first fiber ends 423 and second fiber ends 425 can be arranged with respect to the first detector 437 and the second detector 441 to optimize the detection of the interacted photons corresponding to the first multi-passband wavelengths by the first detector and the interacted photons corresponding to second multi-passband wavelengths by the second detector. Once the first detector 437 and the second detector detect the interacted photons 435, the first detector 437 is configured to generate a first image data set (T1), and the second detector 441 is configured to generate a second image data set (T2). In one embodiment, the first image data set and the second image data set may be further analyzed.

System Having an Acousto-Optic Filter Arrangement

Figure 5:
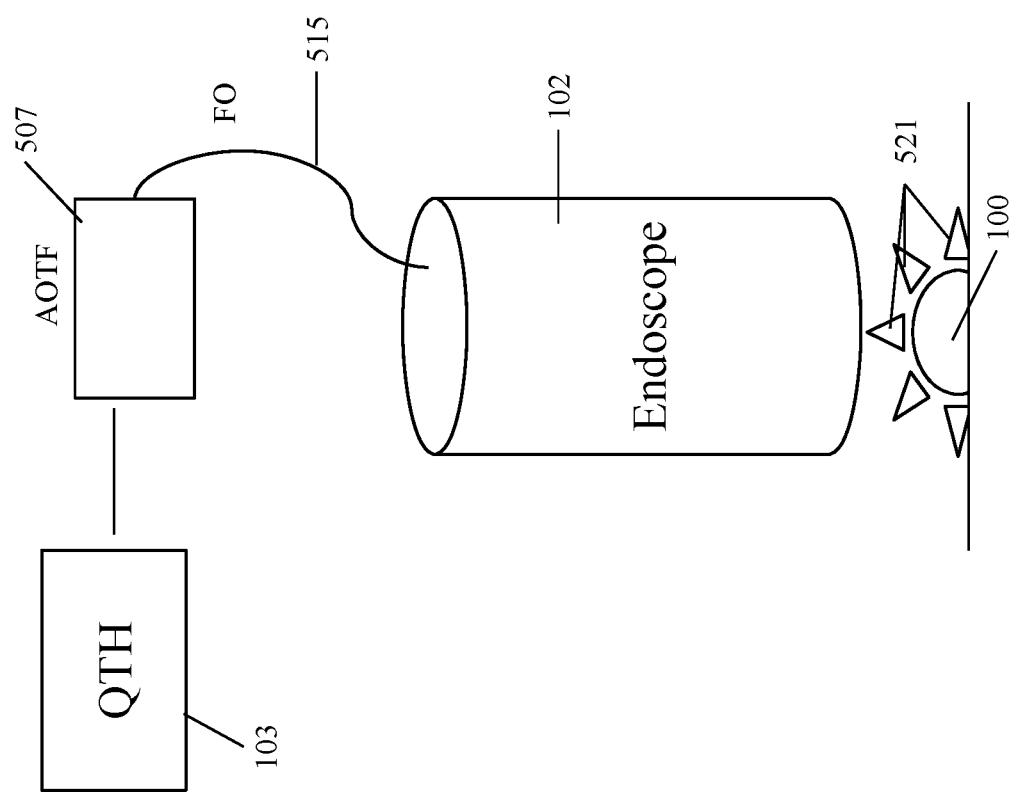
FIG. 5 illustrates an endoscope comprising an imaging system having an acousto-optic filter according to an embodiment.

FIG. 5 illustrates an embodiment of the instant disclosure employing an acousto-optic tunable filter (AOTF). This embodiment features an illumination source 103 to generate illuminating photons for illuminating a sample 100. A filter 507 is configured to filter photons emitted from the illumination source 103. In one embodiment, the filter 507 comprises an AOTF in which the AOTF transmits a single passband wavelength. To achieve a >10 fps sampling rate, the AOTF is rapidly switched between target and background passband wavelengths. In another embodiment, the filter comprises a conformal filter based on AOTF technology in which the AOTF transmits multi-passband wavelengths simultaneously. To switch between T1 and T2 states, the conformal filter AOTF is switched in series with microsecond switching speeds. In other embodiments, multiple conformal AOTFs may be employed in which the T1 and T2 states are selected simultaneously. In embodiments employing multiple acousto-optic filters, each filter may be tuned to various wavelengths where each filter transmits different multi-passband wavelengths simultaneously.

Acousto-optic filters are known in the art and, generally, operate by passing a beam of source light through a substrate, typically quartz. The substrate is vibrated by a piezoelectric transducer modulator. An RF frequency is applied to the modulator, causing the substrate to vibrate. Source light or radiation is passed through the vibrating substrate, which causes the source light passing through the substrate to diffract, thus creating a filter gradient for the source light. The source light emitted from the acousto-optic filter can be filtered to a desired passband wavelength by the RF frequency applied to the piezoelectric transducer. Details on the operation of an acousto-optic filter are described in more detail in Turner, John F. and Treado, Patrick J. "Near-Infrared Acousto-Optic Tunable Filter Hadamard Transform Spectroscopy" *Applied Spectroscopy*, 50.2 (1996), 277-284, which is incorporated by reference herein in its entirety.

Figure 5A:
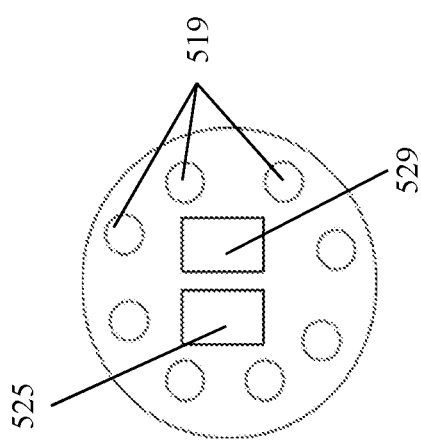
FIG. 5A is an end-on view of the endoscope the embodiment in FIG. 5.

The passband wavelength transmitted from the filter 507 is transmitted to the distal end of an endoscope 102 through a fiber optic bundle 515. FIG. 5A illustrates the distal end of the endoscope 102 and features a plurality of fiber ends 519 from the fiber optic bundle 515. The fiber ends 519 transmit the passband wavelength from the filter 507 to illuminate the sample 100 to produce interacted photons 521 which are detected by a first detector 525 and a second detector 529 located on the distal end of the endoscope 102. In one embodiment, only one detector is used, i.e., the first detector 525, to detect a plurality of the interacted photons 521. In another embodiment, the interacted photons 521 are detected by both detectors 525 and 529. In another embodiment, a plurality of acousto-optic filters are employed and generate a first passband wavelength and a second passband wavelength. The first detector 525 may be configured to detect the first passband wavelength and generate a first image data set (T1), and the second detector 529 may be configured to detect the second passband wavelength and generate a second image data set (T2). In one embodiment, the first image data set and the second image data set may be further analyzed as set forth below.

System Having an MOE Filter Wheel Arrangement

Figure 6:
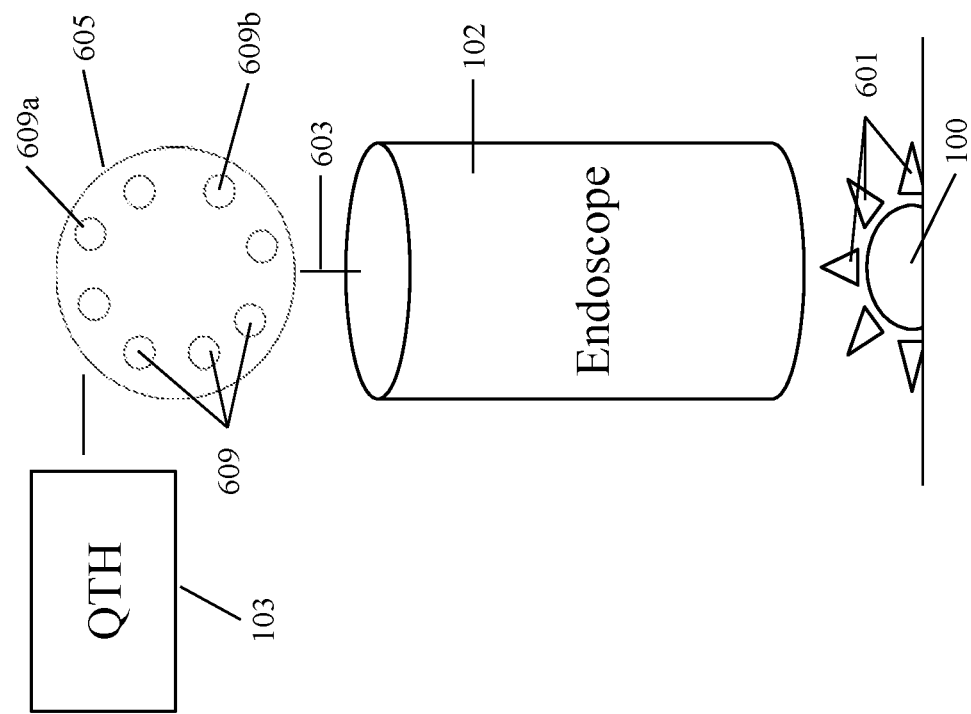
FIG. 6 illustrates an endoscope comprising an imaging system having a MOE filter wheel according to an embodiment.

FIG. 6 illustrates another embodiment according to the instant disclosure. An illumination source 103 generates illuminating photons which are transmitted to a filter wheel 605 where the illuminating photons are filtered to generate filtered photons. The filter wheel 605 comprises a plurality of filter elements 609. In one embodiment, each filter element 609 comprises an MOE. Suitable MOEs for use in the instant disclosure are known in the art and described herein. Each filter element 609 may be different, and each filter element may be configured to filter and transmit a different passband wavelength. For example, filter element 609a may be configured to transmit a wavelength corresponding to a background, such as a specific type of tissue or anatomical structure, and filter element 609b may be configured to transmit a passband wavelength corresponding to an anomaly in a tissue sample, such as a cancerous tumor on the tissue. In this type of embodiment, the filter wheel 605 can be rotated during a surgical procedure to assist a surgeon in distinguishing normal tissue from cancerous tissue. In another embodiment, the filter elements 609 are configured to detect a plurality of different samples. In one embodiment, the filter elements 609 are configured to discriminate background tissue from an anatomical structure such as a ureter.

Figure 6A:
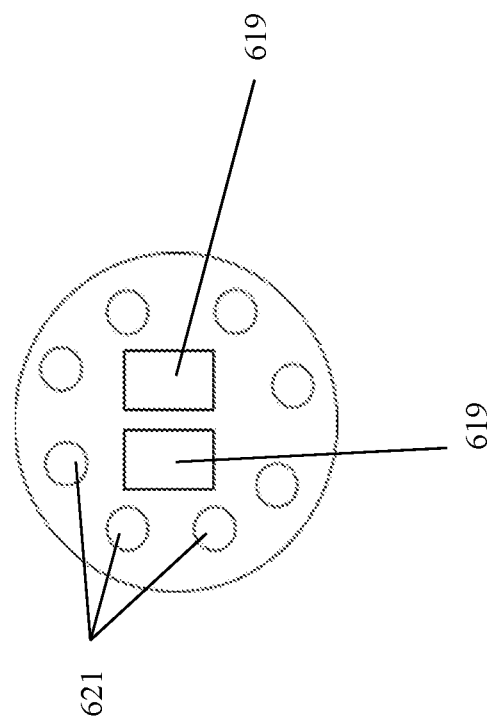
FIG. 6A is an end-on view of the endoscope according to the embodiment in FIG. 6.

The filtered photons are transmitted via a fiber optic bundle 603 to the distal end of the endoscope 102 and exit the distal end of the endoscope through a plurality of fiber ends 621 as shown in FIG. 6A. The filtered photons illuminate the sample 100 and generate a plurality of interacted photons 601. The interacted photons 601 are detected by one or more detectors 619, and the one or more detectors 619 are configured to generate an image data set (T1). In one embodiment, the image data set may be further analyzed, as set forth below.

System Having a Patterned Etalon Filter Arrangement

Figure 7:
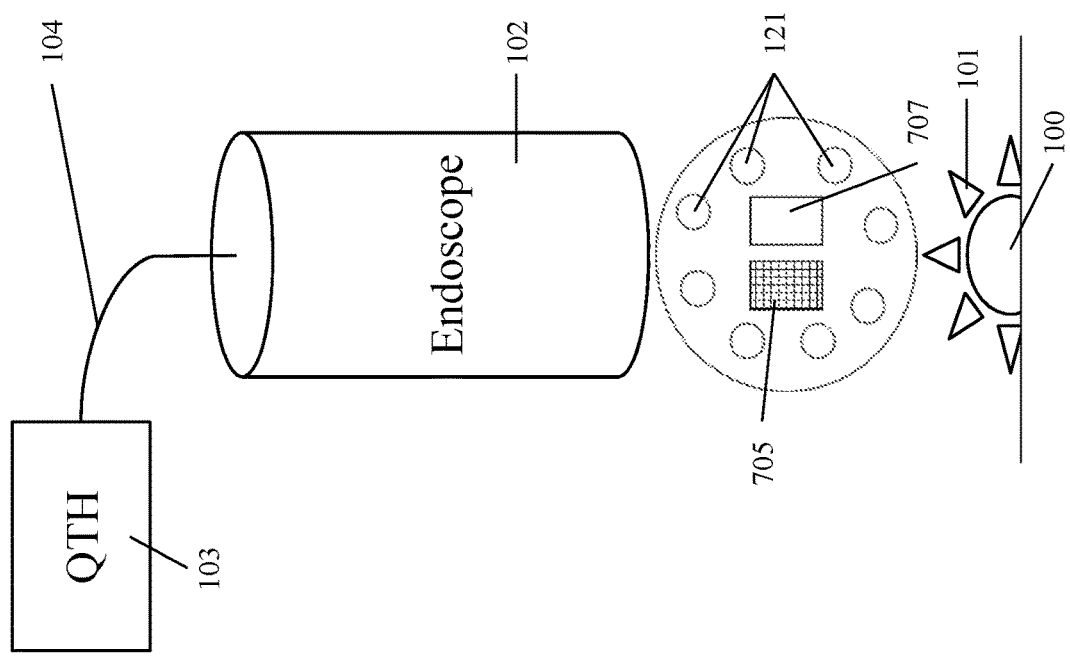
FIG. 7 illustrates an endoscope comprising an imaging system having a patterned etalon filter arrangements according to an embodiment.

FIG. 7 illustrates another embodiment of the instant disclosure. Illumination source 103 generates illuminating photons which are transmitted through a fiber optic bundle 104 to the distal end of the endoscope 102 to fiber ends 121. Illuminating photons exit the fiber ends 121 and illuminate the sample 100 and generate interacted photons 101 from the sample 100. The interacted photons 101 are detected by a first detector 705 and a second detector 707 disposed on the distal end of the endoscope 102. In one embodiment, the first detector 705 and the second detector 707 comprise hyperspectral cameras. In one embodiment, the detectors 705 and 707 comprise a Fabry-Pérot interferometric (patterned etalon) filter configuration disposed on each pixel of the detector. Suitable examples of patterned etalon filter arrangements and associated detectors are available from Ximea Corporation. The filter on each pixel is configured to transmit one or more passband wavelengths for each pixel. In one embodiment, the first detector 705 comprises a patterned etalon filter arrangement in a mosaic snapshot arrangement. A mosaic snapshot can be acquired over 1088× 2048 pixels. In one embodiment, the mosaic snapshot comprises a 4×4 mosaic having 16 wavelength bands. In another embodiment, the mosaic snapshot comprises a snapshot of the sample from 465-630 nm at 11 nm intervals. In another embodiment, the mosaic snapshot may comprise a 5×5 mosaic having 25 bands over a wavelength range from about 600 to 1,000 nm. The mosaic snapshot may include a spatial resolution per band of about 512×272 with up to 2 megapixels with interpolation and may collect up to 170 datacubes/sec.

In another embodiment, the first detector 705 and the second detector 707 may comprise a patterned etalon filter arrangement for obtaining a snapshot tiled configuration. In one embodiment, the snapshot tiled configuration transmits a passband wavelength at each pixel. The patterned etalon snapshot tiled filter configuration can acquire up to 1088× 2048 pixels. In one embodiment, the tiled snapshot has a spectral resolution of up to 32 bands and can detect wavelengths ranging from 600-1,000 nm over 12 incremental steps. In another embodiment, the spatial resolution per band is about 256×256. In another embodiment, the tiled snapshot may detect up to 170 data-cubes/sec. The patterned etalon filter arrangement may also be customized to generate a predetermined response based on the sample to be analyzed and the result desired. Such customization would be apparent to one of skill in the art in view of this disclosure. In still further embodiments, the patterned etalon filters are tuneable.

In one embodiment, the first detector 705 and the second detector 707 comprise IMEC mosaic filter arrangements. In such an embodiment, the patterned etalon mosaic filter arrangements of the first detector 705 and the second detector 707 are configured to transmit one or more different wavelength bands at each pixel. In another embodiment, the first detector 705 and the second detector 707 comprise patterned etalon tiled filter arrangements. In such an embodiment, the patterned etalon tiled filter arrangements of the first detector 705 and the second detector 707 are configured to detect a different wavelength band at each pixel. In another embodiment, the second detector is eliminated, and the embodiment employs the first detector 705 having either a snapshot mosaic patterned etalon filter arrangement or a snapshot tiled patterned etalon filter arrangement.

The detectors 705 and 707 are configured to generate one or more image data sets for each passband wavelength transmitted from the filter arrangements. In one embodiment, the detectors 705 and 707 are configured to generate a first image data set (T1) and a second image data set (T2). In one embodiment, the image data sets may be further analyzed, as set forth below.

Other Features

In yet another embodiment, an illumination source may be configured to generate illuminating photons at specific wavelengths. For example, the illumination source may comprise a plurality of LEDs, where a first portion of the LEDs are configured to generate a first wavelength and a second portion of the LEDs are configured to generate a second wavelength for illuminating a sample. In such an embodiment, a first detector may be configured to detect interacted photons from the first wavelength and generate a first image data set (T1), and a second detector may be configured to detect interacted photons from the second wavelength and generate a second image data set (T2). Other illumination sources or arrangements may be employed which are capable of producing illuminating photons at a plurality of wavelengths. In one embodiment, the illumination source comprises a modulating laser which is capable of generating multiple wavelengths.

The image data sets described herein may comprise one or more of an ultraviolet (UV) image data set, fluorescence image data set, a visible (VIS) image data set, a Raman image data set, a near-infrared (NIR) image data set, a short-wave infrared (SWIR) data set, a mid-infrared (MIR) data set, and a long-wave infrared (LWIR) data set. In another embodiment, the image data set comprises a hyperspectral image data set. The image data sets of the instant disclosure may be further analyzed. In one embodiment, the systems disclosed herein may include a fiber array spectral translator (FAST). Suitable FAST devices are disclosed in U.S. Pat. No. 8,098,373 to Nelson et al., entitled SPATIALLY AND SPECTRALLY PARALLELIZED FIBER ARRAY SPECTRAL TRANSLATOR SYSTEM AND METHOD OF USE, filed Apr. 13, 2010 and assigned to ChemImage Corporation, the disclosure of which is incorporated herein by reference in its entirety.

In one embodiment, the filter can be a multi-conjugate liquid crystal tunable filter (MCF). An MCF includes a series of stages composed of polarizers, retarders, and liquid crystals. As a result of this arrangement, the MCF is capable of providing diffraction-limited spatial resolution and spectral resolution consistent with a single stage dispersive monochromator. The MCF may be tuned to any wavelength in the given filter range. In some embodiments, the MCF may be controlled by a processor.

In one embodiment, the systems disclosed herein may comprise a processor and a non-transitory processor-readable storage medium in operable communication with the processor. The storage medium may contain one or more programming instructions that, when executed, cause the processor to analyze the image data sets. In one embodiment, the analysis may comprise applying an optical computation to the data set. In another embodiment, the optical computation may comprise one or more of T1 and (T1−T2)/(T1+T2). Other optical computations known in the art may be applied. In one embodiment, the analysis may comprise applying one or more chemometric techniques to the image data sets. The chemometric analysis may comprise one or more of a multivariate curve resolution analysis, a principle component analysis (PCA), a partial least squares discriminant analysis (PLSDA), a k-means clustering analysis, a band t entropy analysis, an adaptive subspace detector analysis, a cosine correlation analysis, a Euclidian distance analysis, a partial least squares regression analysis, a spectral mixture resolution analysis, a spectral angle mapper metric analysis, a spectral information divergence metric analysis, a Mahalanobis distance metric analysis, and spectral unmixing analysis. In some embodiments, the processor may be configured to control operation of the system. For example, in embodiments where a tunable filter is employed, the process may be configured to cause the processor to apply voltages to the tunable filter to obtain the desired passband transmission. Further, the processor may be configured to control timing of an illumination source and detectors so that the correct detector is in operation for the specific illumination. Other processor configurations are contemplated and would be apparent to one of skill in the art in view of this disclosure.

The systems according to the instant disclosure may further include a display. In some embodiments, the display may provide one or more results from one or more of the detectors. In another embodiment, the display may provide one or more results from the analysis of the processor. In one embodiment, the display may provide one or more results from one or more of the detectors and one or more results from the analysis of the processor.

The systems and methods of the disclosure may further include simultaneous processing of images from multiple spectral ranges. In one embodiment, images generated in the visible range as a Red Green Blue (RGB) image are processed with images generated from the UV range. In another embodiment, images generated in the visible range as an RGB image are processed with images generated from the SWIR or NIR range. In another embodiment, images generated in the visible range as an RGB image are processed with images generated in the visible range with molecular chemical imaging (MCI).

EXAMPLES

Bile duct calculi removed from human patients were placed in various locations within the biliary system of domestic pig (swine). The bile duct calculi were of two types: those formed of cholesterol which were typically yellow or green in color, and those formed of "pigment" which were black or brown. Key anatomical locations of the biliary system were annotated in the Red Green Blue (RGB) images taken of the biliary system. Locations of the bile duct calculi were also annotated in the RGB images to show the ground truth. Key anatomical locations include the liver, gallbladder, cystic duct, fat, common bile duct, pancreas, and vena cava.

Data was collected by the HSI EXAMINER 200QD ("Examiner") available from ChemImage Corporation of Pittsburgh, Pennsylvania which is an example of one embodiment of the system of the disclosure that is not intended to be limiting. The Examiner includes a high-definition RGB camera (3.1 megapixel, 8-bit RGB color) and a hyperspectral camera (1.4 megapixel, 14-bit). Sensing modalities include diffuse reflectance/absorbance using two 150 watt quartz tungsten halogen flood lamps; oblique reflectance illumination; transmittance using one 150 watt quartz tungsten halogen lamp; luminescence using a tunable excitation light source of filtered 250 watt quartz tungsten halogen light source and independent long and short pass filters; luminescence using ultraviolet excitation light sources in the UV-A (368 nm), UV-B (306 nm), and UV-C (253 nm) ranges; optical variable device (OVD) angle-sensitive illumination using horizontal and vertical white light and UV (365 nm) LED lighting. For broadband luminescence imaging, the seven high pass filters are for the wavelengths 400 nm, 450 nm, 500 nm, 550 nm, 600 nm, 650 nm, 700 nm, and the two short pass filters are for wavelengths of 700 nm and 750 nm. The device includes dual visible and near infrared (NIR) liquid crystal tunable filters (LCTF) and operates in the 400 nm-1100 nm spectral range with tuning increments of 1 nm-20 nm step size acquisitions. The spectral resolution is 4 nm-10 nm bandpass (FWHM) and a 7 nm average bandpass. The device also has a motorized zoom optical magnification of 0.5× to 0.62× with a ground sample distance of 10.4 μm/pixel at 0.62× magnification. Field of view is 163 mm×124 mm×13 mm×10 mm and a resolution of 600 dpi is achieved in the collection optic. Detection time is approximately 2-5 minutes for white light hyperspectral acquisitions and 5-30 minutes for luminescence hyperspectral acquisitions.

Figure 8:
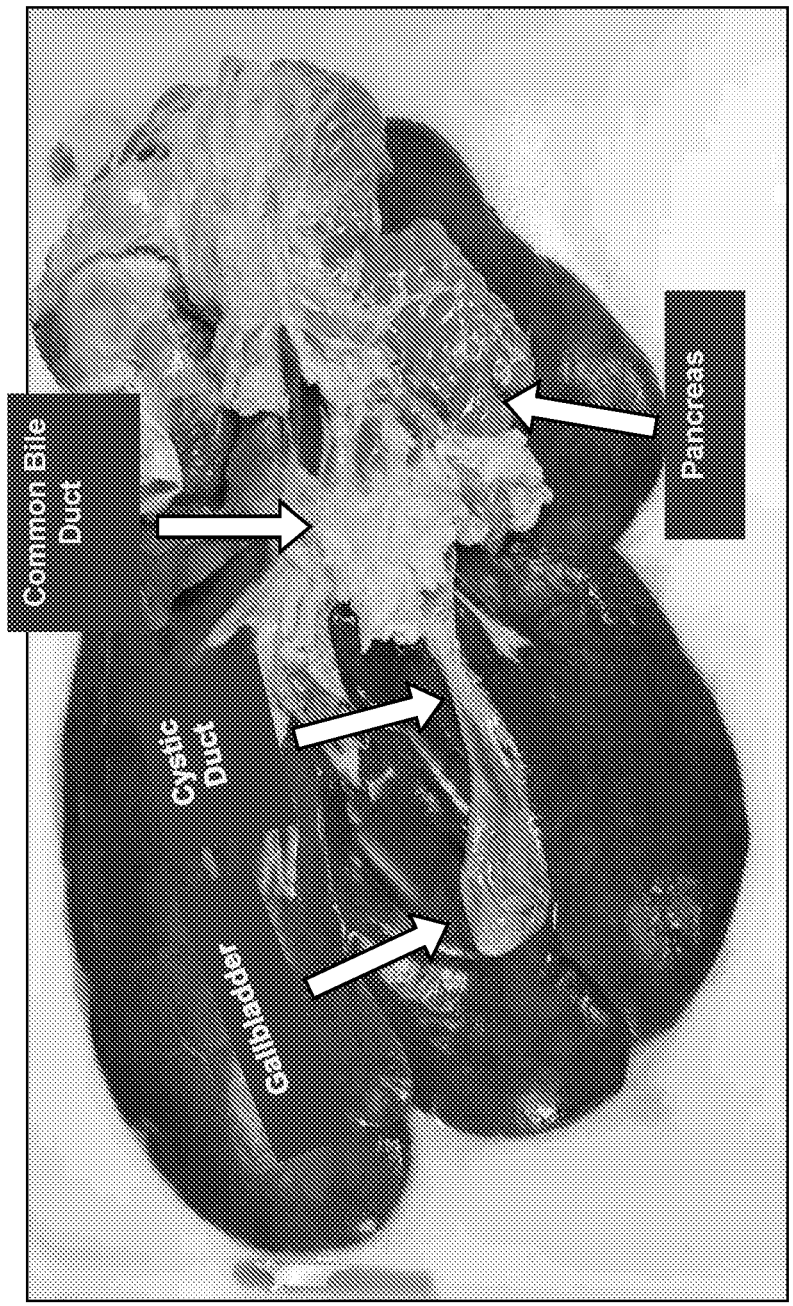
FIG. 8 is a an annotated photograph of a biliary system removed from a domestic pig.

During experiments, the calculi were placed inside the gallbladder, inside the cystic duct, inside the common bile duct, and inside the pancreas. FIG. 8 shows an annotated photograph of a biliary system removed from a domestic pig, which includes the different anatomical locations of the domestic pig swine, which are anatomically similar and representative of a human biliary tract. Calculi were placed in separate imaging tests so that they were obscured by the gallbladder, cystic duct, common bile duct, and pancreas. Each location was then imaged by the Examiner using visible and NIR molecular chemical imaging techniques to determine the detectable level of contrast.

Figure 9B:
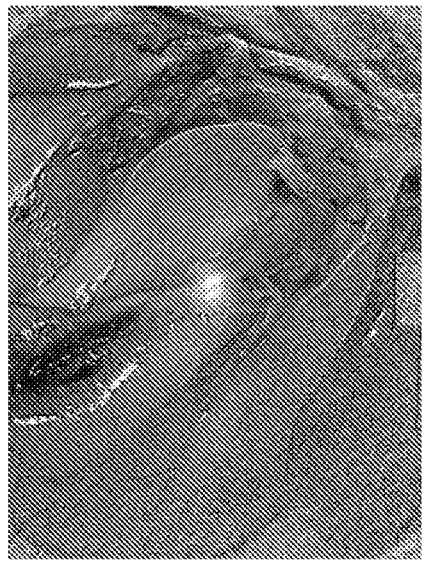
FIG. 9B includes two images that are the score image and the RGB image and overlaid detection of a calculus obscured by the cystic duct of a biliary system removed from a domestic pig.
Figure 9B:
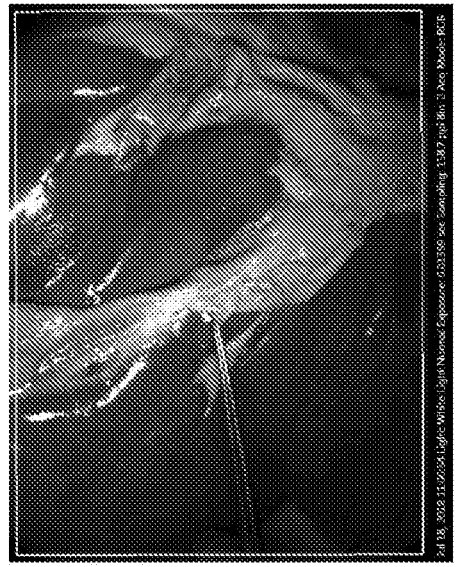
Figure 9A:
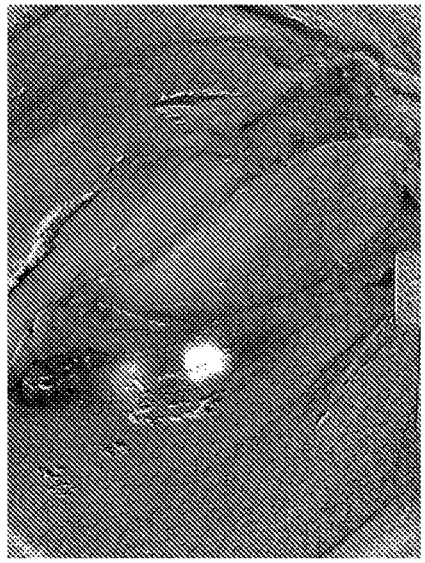
FIG. 9A includes two images that are the score image and the RGB image and overlaid detection of a calculus obscured by the gallbladder of a biliary system removed from a domestic pig.
Figure 9A:
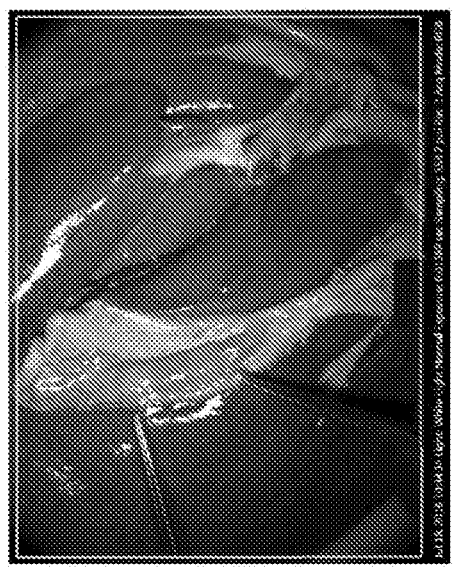

FIG. 9A includes two images obtained from calculi obscured by the gallbladder of the above biliary system. The first image is a score image generated from hypercubes collected with the Examiner when analyzing for contrast between the calculi and the surrounding tissue when obscured by the gallbladder and is not enhanced by combination with a RGB image. Because the calculi have a different chemical makeup than the surrounding tissue, the top image shows the calculi as bright white against the surrounding darker gray tissue. The bottom image is the same image but combined and processed by image processing techniques with a corresponding RGB image. Detections are generated from the score images, and the detections define the border of the target tissue, for example, a calculus. The detection is colored to distinguish it when it is overlaid onto a RGB image. The detections, which represent calculi are highlighted in a green color for increased visibility and contrast.

Figure 9D:
FIG. 9D includes two images that are the score image and the RGB image and overlaid detection of a calculus obscured by the pancreas of the biliary system removed from a domestic pig.
Figure 9D:
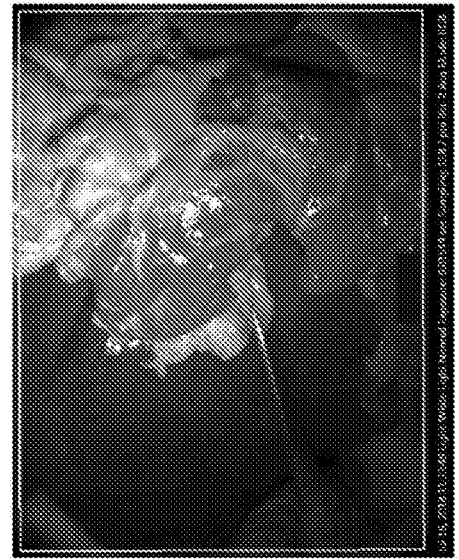
Figure 9C:
FIG. 9C includes two images that are the score image and the RGB image and overlaid detection of a calculus obscured by the common bile duct of a biliary system removed from a domestic pig.
Figure 9C:
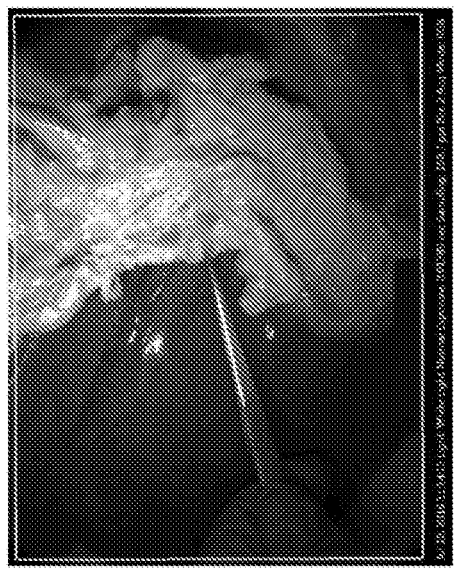

FIGS. 9B, 9C, and 9D are similar and show calculi that are obscured by the cystic duct (FIG. 9B), common bile duct (FIG. 9C), and pancreas (FIG. 9D), respectively. In each, the top image is taken when analyzing for contrast between the calculi and surrounding tissue when obscured and not enhanced by combination with a RGB image. Also, the bottom image of each is the same image but combined and processed by image processing techniques with a corresponding RGB image. Similar to the discussion above, the detections that represent calculi are highlighted in a green color for increased visibility and contrast.

Figure 10:
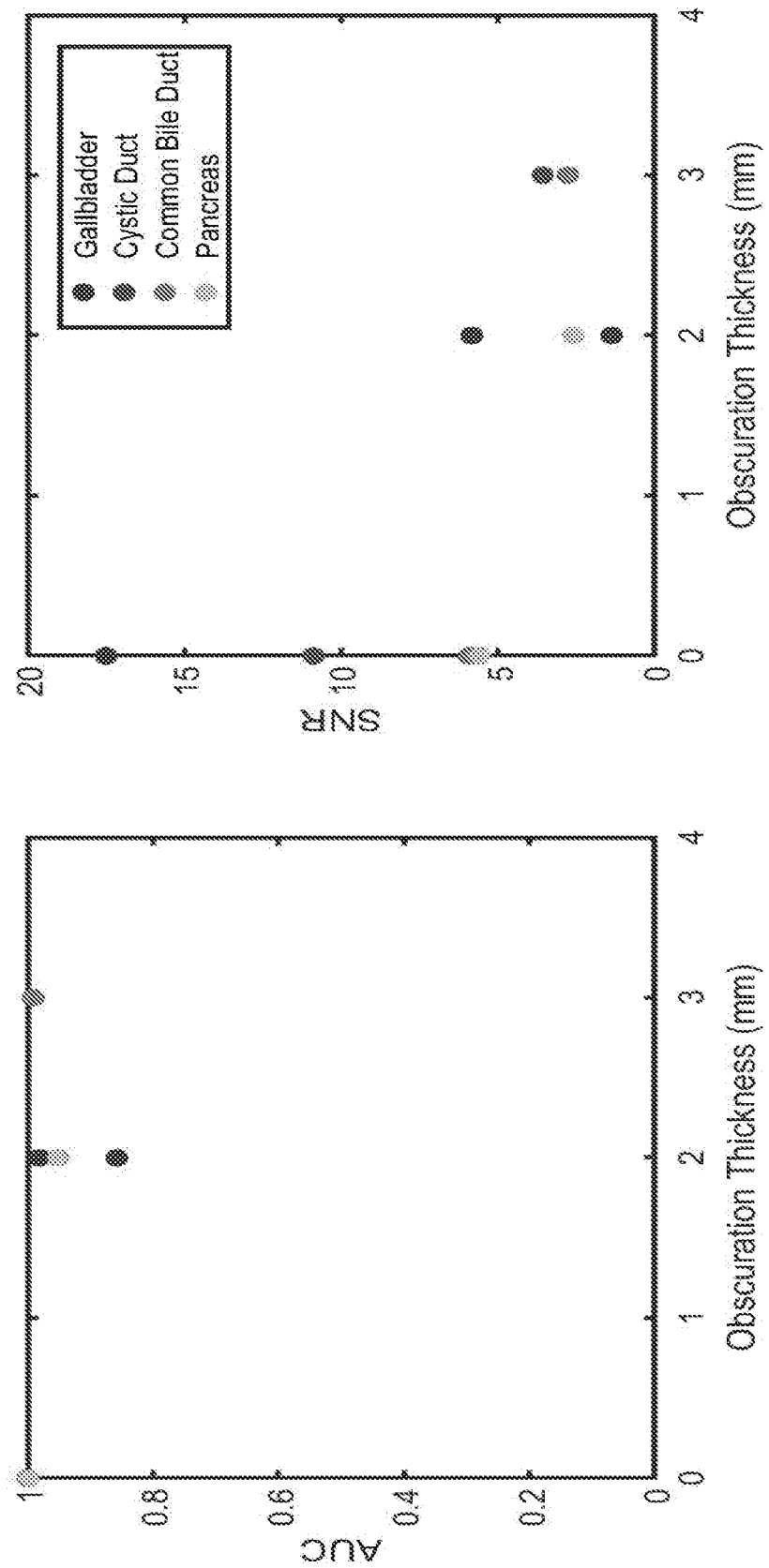
FIG. 10 is a plot of the Area Under Curve (AUC) and signal to noise ratio (SNR) versus obscuration thickness in millimeters for results having a consistent case score of 970/800 and plotted for calculi that are obscured by the gallbladder, cystic duct, common bile duct, and pancreas.

In further experiments, samples were selected that had a consistent case score when measured with first and second photons of 970 nm and 800 nm wavelengths. In these tests, good contrast between the calculi and surrounding tissue was observed, though good contrast was also observed when testing first and second photons of 545 nm and 715 nm wavelengths, respectively. FIG. 10 graphically depicts the results of these tests. In the left-most plot of FIG. 10, the area under curve (AUC) versus the obscuration thickness in millimeters for results having a consistent case score of 970 nm/800 nm is disclosed. The obscuration thickness is a measurement of the thickness of the tissue that obscures the calculus, i.e., imaging a given calculus with a higher obscuration thickness is expected to be more challenging to analyze. In the right-most plot of FIG. 10, the signal to noise ratio (SNR) versus the obscuration thickness in millimeters for results having a consistent case score of 970 nm/800 nm is disclosed. Again, a larger obscuration thickness indicates a more challenging sample to analyze. While the AUC and SNR do in some instances decline with increasing obscuration thickness, the tests demonstrate that even with up to 3 mm of obscuring tissue, calculi can be detected using the systems and methods of the disclosure.

Figure 11B:
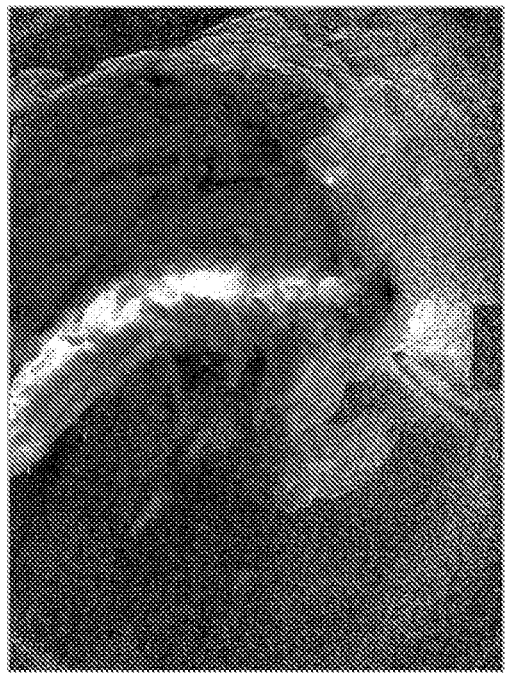
FIG. 11B is a score image of the common bile duct from surrounding tissue.
Figure 11A:
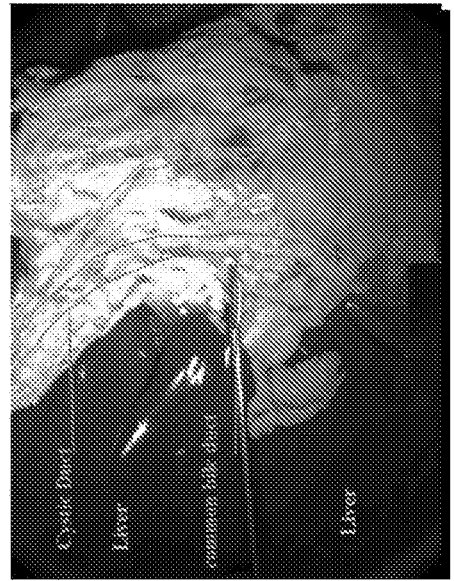
FIG. 11A is a red green blue (RGB) image of a sample used during experiments for discriminating the common bile duct from surrounding tissue.
Figure 11C:
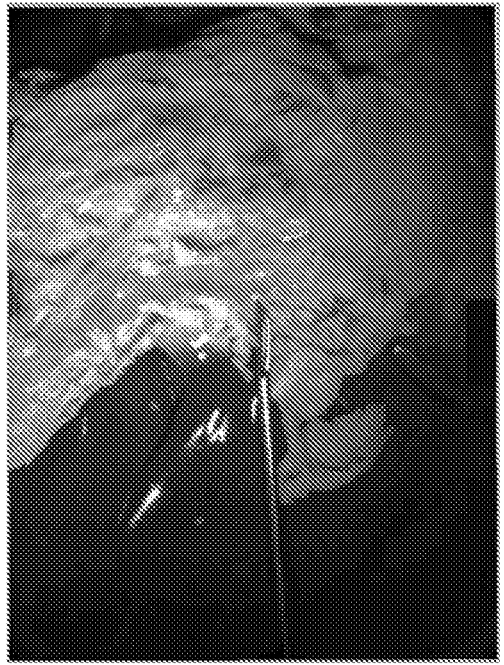
FIG. 11C is a is a detection of the common bile duct, overlaid onto the RGB image of the common bile duct.

In still further experiments, samples were selected and analyzed to determine performance in distinguishing between ducts and surrounding tissues. For this, a domestic pig biliary tract was used to test identification of the common bile duct from surrounding tissue. FIG. 11A shows an annotated RGB image of a sample area which was used in the experiment. FIG. 11B shows the score image formed the biliary system was analyzed, and FIG. 11C shows the result of image processing and combining the RGB image with the score image, with areas of contrast highlighted in green for visibility. In some embodiments, at least one detection image is overlaid onto at least one RGB image.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. An imaging system for discriminating a calculus from surrounding tissue, comprising:
    an illumination source configured to generate illuminating photons;
    a first filter configured to filter a first plurality of illuminating photons and generate a first plurality of filtered photons comprising first multi-passband wavelengths and a second filter configured to filter a second plurality of illuminating photons and generate a second plurality of filtered photons comprising second multi-passband wavelengths, wherein a sample is illuminated with the first plurality of filtered photons and the second plurality of filtered photons to generate a first plurality of interacted photons and a second plurality of interacted photons, respectively; and
    one or more detectors configured to detect the first plurality of interacted photons and the second plurality of interacted photons and generate one or more image data sets; and
    a processor that processes the one or more image data sets and generates, using a multivariate algorithm, information related to a location of a calculus with respect to surrounding tissue,
    wherein the processor is configured to generate one or more hypercubes from the one or more image data sets and generate a score image using the one or more hypercubes, and
    wherein the first filter and the second filter are configured to filter the first plurality of illuminating photons and the second plurality of illuminating photons simultaneously.

2. The imaging system of claim 1, wherein the information related to the location of a calculus with respect to surrounding tissue is a visual image.

3. The imaging system of claim 2, wherein the processor colorizes regions corresponding to the calculus in the visual image thereby increasing visual contrast between the calculus and surrounding tissue.

4. The imaging system of claim 1, wherein the imaging system is an endoscope.

5. An imaging system for discriminating a calculus from surrounding tissue, comprising:
    an illumination source configured to illuminate a calculus and surrounding tissue to thereby generate interacted photons;
    a first filter configured to filter a first plurality of the interacted photons and transmit first multi-passband wavelengths and a second filter configured to filter a second plurality of interacted photons and transmit second multi-passband wavelengths;
    one or more detectors configured to detect the first multi-passband wavelengths and the second multi-passband wavelengths and generate one or more image data sets of the first passband wavelengths and the second passband wavelengths; and
    a processor that processes the one or more image data sets and generates information related to the location of a calculus with respect to surrounding tissue,
    wherein the processor is configured to generate one or more hypercubes from the one or more image data sets and generate a score image using the one or more hypercubes,
    wherein the first filter and the second filter are configured to filter the first plurality of interacted photons and the second plurality of interacted photons simultaneously, and wherein the one or more image data sets comprise a RGB image in the visible range and a molecular chemical image in the visible range.

6. The imaging system of claim 5, wherein the information related to the location of a calculus with respect to surrounding tissue is a visual image.

7. The imaging system of claim 6, wherein the processor colorizes regions corresponding to the calculus in the visual image thereby increasing visual contrast between the calculus and surrounding tissue.

8. The imaging system of claim 5, wherein the imaging system is an endoscope.

9. A method of discriminating a calculus from surrounding tissue, comprising:
   generating illuminating photons;
   filtering, by a first filter, a first plurality of illuminating photons and generating a first plurality of filtered photons comprising first-multi-passband wavelengths and filtering, by a second filter, a second plurality of illuminating photons and generating a second plurality of filtered photons comprising second multi-passband wavelengths, wherein a sample is illuminated with the first plurality of filtered photons and the second plurality of filtered photons to generate a first plurality of interacted photons and a second plurality of interacted photons, respectively; and
   detecting a first plurality of interacted photons and the second plurality of interacted photons and generating a first image data set and a second image data set simultaneously; and
   processing the first image data set and the second image data set and generating, using a multivariate algorithm, information related to a location of a calculus with respect to surrounding tissue,
   wherein the processing comprises generating one or more hypercubes from the first image data set and the second image data set and generating a score image using the one or more hypercubes, and
   wherein the first filter and the second filter are configured to filter the first plurality of illuminating photons and the second plurality of illuminating photons simultaneously.

10. The method of claim 9, wherein the method takes place during surgery.

11. A method of discriminating a calculus from surrounding tissue, comprising:
   illuminating a calculus and surrounding tissue to thereby generate interacted photons;
   filtering, by a first filter, a first plurality of the interacted photons and transmitting first multi-passband wavelengths and filtering, by a second filter, a second plurality of interacted photons and transmitting second multi-passband wavelengths;
   detecting the first multi-passband wavelengths and the second multi-passband wavelengths and generating a first image data set of the first passband wavelengths and a second image data set of the second passband wavelengths simultaneously; and
   processing the first image data set and the second image data set and generating, using a multivariate algorithm, information related to the location of a calculus with respect to surrounding tissue, wherein the processing comprises generating one or more hypercubes from the first image data set and the second image data set and generating a score image using the one or more hypercubes,
   wherein the first filter and the second filter are configured to filter the first plurality of interacted photons and the second plurality of interacted photons simultaneously, and
   wherein the first image data set and the second image data set comprise a RGB image in the visible range and a molecular chemical image in the visible range, respectively.

12. The method of claim 11, wherein the method takes place during surgery.

* * * * *